(12) United States Patent
Marnfeldt et al.

(10) Patent No.: US 9,174,051 B2
(45) Date of Patent: Nov. 3, 2015

(54) REAL TIME COMPLIANCE VOLTAGE GENERATION FOR AN IMPLANTABLE STIMULATOR

(71) Applicant: Boston Scientific Neuromodulation Corporation, Valencia, CA (US)

(72) Inventors: Goran N. Marnfeldt, Valencia, CA (US); David K. Peterson, Valencia, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/848,270

(22) Filed: Mar. 21, 2013

(65) Prior Publication Data

US 2013/0289665 A1   Oct. 31, 2013

Related U.S. Application Data

(60) Provisional application No. 61/654,606, filed on Jun. 1, 2012, provisional application No. 61/639,991, filed on Apr. 29, 2012.

(51) Int. Cl.
| | |
|---|---|
| *A61N 1/36* | (2006.01) |
| *A61N 1/378* | (2006.01) |
| *A61N 1/37* | (2006.01) |

(52) U.S. Cl.
CPC ........ *A61N 1/36128* (2013.01); *A61N 1/36125* (2013.01); *A61N 1/3782* (2013.01); *A61N 1/3706* (2013.01)

(58) Field of Classification Search
CPC . A06N 1/36128; A61N 1/378; A61N 1/3782; H02M 3/07; H02M 2001/009; H02M 3/156

USPC ............................................................. 607/74
See application file for complete search history.

(56) References Cited

U.S. PATENT DOCUMENTS 6,201,234 B1 * 3/2001 Chow et al. ............. 250/214 LS
6,289,246 B1 * 9/2001 Money ............................ 607/56
(Continued)

FOREIGN PATENT DOCUMENTS

| WO | 0021607 A1 | 4/2000 |
|---|---|---|
| WO | 2007070727 A1 | 6/2007 |
| WO | 2010096131 A1 | 8/2010 |

OTHER PUBLICATIONS

Emilia Noorsal et al : "A Neural Stimulator Frontend With High-Voltage Compliance and Programmable Pulse Shape for Epiretinal Implants", IEEE Journal of Solid-State Circuits, IEEE Service Center, Piscataway, NJ, USA, vol. 47, No. I, Jan. 1, 2012.
(Continued)

*Primary Examiner* — Carl H Layno
*Assistant Examiner* — Erin Piateski
(74) *Attorney, Agent, or Firm* — Lewis & Reese, PLLC

(57) ABSTRACT

Circuitry for generating a compliance voltage (V+) for the current sources and/or sinks in an implantable stimulator device is disclosed. The improved compliance voltage generation circuitry adjusts V+ to an optimal value in real time, even during the provision of a stimulation current. The circuitry uses amplifiers to measure the voltage drop across an active PDACs (current sources) and/or NDAC (current sinks) The measured voltages are input to a V+ regulator, which compares the measured voltage drops across the DACs to optimal values, and which feeds an optimized value for V+ back to the DACs in real time to keep the voltage drop(s) at those optimal levels during the stimulation current for efficient DAC operation.

18 Claims, 23 Drawing Sheets

(56) References Cited

U.S. PATENT DOCUMENTS

| | | | |
|---|---|---|---|
| 6,317,628 B1 * | 11/2001 | Linder et al. | 600/547 |
| 6,442,422 B1 * | 8/2002 | Duckert | 600/547 |
| 7,177,698 B2 | 2/2007 | Klosterman et al. | |
| 7,235,050 B2 * | 6/2007 | Schulman et al. | 600/300 |
| 7,444,181 B2 | 10/2008 | Shi et al. | |
| 7,483,748 B2 | 1/2009 | Torgerson et al. | |
| 7,539,538 B2 | 5/2009 | Parramon et al. | |
| 7,890,182 B2 | 2/2011 | Parramon et al. | |
| 8,131,377 B2 | 3/2012 | Shi et al. | |
| 2002/0072770 A1 * | 6/2002 | Pless | 607/2 |
| 2002/0077670 A1 * | 6/2002 | Archer et al. | 607/45 |
| 2005/0226019 A1 * | 10/2005 | Nastase | 363/141 |
| 2006/0066379 A1 * | 3/2006 | Hopsecger | 327/306 |
| 2007/0100399 A1 | 5/2007 | Parramon et al. | |
| 2007/0135868 A1 * | 6/2007 | Shi et al. | 607/62 |
| 2008/0136386 A1 * | 6/2008 | Nastase | 323/275 |
| 2008/0319497 A1 | 12/2008 | Griffith et al. | |
| 2008/0319514 A1 * | 12/2008 | Shi et al. | 607/62 |
| 2009/0018618 A1 * | 1/2009 | Parramon et al. | 607/60 |
| 2009/0316743 A1 * | 12/2009 | Alfrey | 372/38.04 |
| 2010/0211132 A1 * | 8/2010 | Nimmagadda et al. | 607/60 |
| 2011/0121801 A1 * | 5/2011 | Scaldaferri et al. | 323/276 |
| 2012/0095529 A1 | 4/2012 | Parramon et al. | |
| 2012/0239108 A1 * | 9/2012 | Foutz et al. | A61N 1/378 607/45 |

OTHER PUBLICATIONS

International Search Report and Written Opinion regarding application No. PCT/US2013/033638 dated May 8, 2013.

* cited by examiner

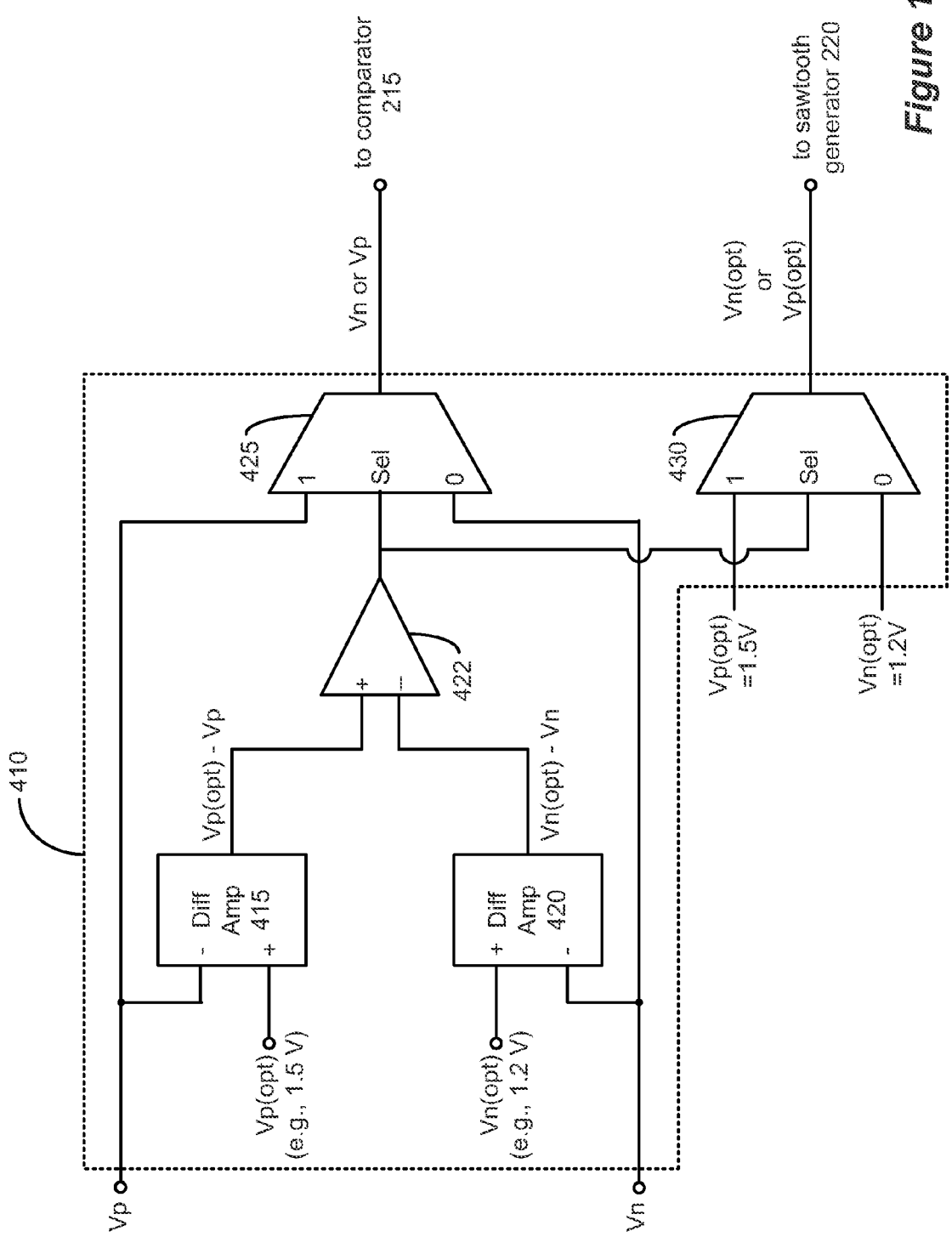

REAL TIME COMPLIANCE VOLTAGE GENERATION FOR AN IMPLANTABLE STIMULATOR

CROSS REFERENCE TO RELATED APPLICATIONS

This application claims priority to U.S. Provisional Patent Application Ser. No. 61/654,606, filed Jun. 1, 2012, and to Ser. No. 61/639,991, filed Apr. 29, 2012, which are both incorporated herein by reference in their entireties.

FIELD OF THE INVENTION

The present invention relates to implantable stimulators, and in particular to circuitry for generating a compliance voltage for the current sources and/or sinks that produce stimulation currents.

BACKGROUND

Implantable stimulation devices generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227. However, the present invention may find applicability in any implantable stimulator.

As shown in FIGS. 1A-1C, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102, 104 couple to the IPG 100 using lead connectors 38a and 38b, which are fixed in a non-conductive header material 36, which can comprise an epoxy for example.

As shown in the cross-section of FIG. 1C, the IPG 100 typically includes an electronic substrate assembly including a printed circuit board (PCB) 16, along with various electronic components 20 mounted to the PCB 16, some of which are discussed subsequently. Two coils (more generally, antennas) are generally present in the IPG 100: a telemetry coil 13 used to transmit/receive data to/from an external controller, and a charging coil 18 for charging or recharging the IPG's battery 26 using an external charger. In this example, the telemetry coil 13 and charging coil 18 are within the case 30, as disclosed in U.S. Patent Publication 2011/0112610. (FIG. 1B shows the IPG 100 with the case 30 removed to ease the viewing of the two coils 13 and 18). However, the telemetry coil 13 may also be mounted within the header 36 of the IPG 100 (not shown).

FIGS. 2A and 2B show different current distribution architectures for forming pulses at the electrodes in an IPG 100. FIG. 2A shows an architecture in which each electrode is provided with a dedicated current source (PDAC 50) and current sink (NDAC 60), such as is disclosed in U.S. Pat. No. 6,181,969 for example. The PDAC 50 and NDAC 60 are so named because the amplitude of the analog current they source or sink is digitally controllable (hence, they are Digital-to-Analog Converters, or DACs), and because they are typically made from P-channel and N-channel transistors respectively. As described in U.S. Pat. No. 7,444,181, which is incorporated by reference in its entirety, the PDACs and NDACs can comprise current mirrors, each of which contains at least one output transistor(s) coupled in parallel to set the desired current.

The architecture of FIG. 2A can be used to pass current between any of the N electrodes. For example, and as illustrated, PDAC 50-1 has been programmed to source a constant stimulation current of Iout, while NDAC 60-2 has been enabled to sink a constant current also equal to Iout. The other PDACs and NDACs are disabled in this example. This results in Iout passing out of electrode E1, through the patient's tissue (not shown), and returning back through electrode E2. More than one PDAC 50 or NDAC 60 can enabled at one time to provide more complicated currents in the patient's tissue. As one skilled in the art understands, stimulation currents are typically issued in the form of pulses, which may be uniphasic or biphasic. Any of the electrodes E1-EN can be chosen to either source or sink current.

FIG. 2B shows a distributed architecture in which sourced or sunk current are passed to or from the electrodes using switch matrices 70P and 70N, such as is disclosed in U.S. Patent Publication 2007/0038250 for example. Switching matrix 70P is controllable to source current from any of the PDACs 50 to any of the electrodes, while switching matrix 70N is controllable to sink current from any of the electrodes via NDACs 60. In the example shown, which also involves sending a stimulation current of Iout from E1 to E2, switching matrix 70P has coupled PDAC 50-2 to E1, while switching matrix 70N has coupled NDAC 60-1 to E2. The switching matrices can also be used to source or sink current to more than one electrode, and the sourced or sunk current from multiple PDACs 50 or NDACs 60 can be sent to the same electrode. Some distributed architectures may only employ a single PDAC 50 and NDAC 60.

Both of the architectures employ decoupling capacitors C1-CN coupled to each of the electrodes. As is well known, decoupling capacitors C1-CN acts as a safety measure to prevent direct DC current injection into the patient.

Regardless of the architecture used, it is important to set the compliance voltage V+ to appropriate levels. The compliance voltage V+ comprises the power supply voltage used by the DAC circuitry that issues the pulses. V+ is generated by boosting the battery voltage, Vbat, and it is desired that V+ be set to an optimal level for the current that that the DACs must provide: if too low, the electrodes will not be able to issue pulses of the desired amplitudes; if too high, battery power is unnecessarily wasted.

One approach to setting V+ is disclosed in U.S. Pat. No. 7,444,181, which is summarized here in FIGS. 3 and 4. In the '181 patent, the voltage drops across the active PDACs (Vp1, Vp2, etc.) and NDACs (Vn1, Vn2, etc.) are measured and used to set V+. This occurs by selecting a tap connected to one of the active DACs using a switching matrix 75. The voltage on the selected tap is sent to an Analog-to-Digital (A/D) converter 80, and the digitized value is sent to and stored in control circuitry 85 (e.g., a microcontroller). Because the control circuitry 85 knows a priori the voltage on the other sides of the DACs (V+ for the PDACs, and ground for the NDACs), the voltage drops Vp and Vn can be determined using the digitized tap values.

Operating within the control circuitry is a V+ algorithm 90, which assesses the voltage drops across the active PDACs and NDACs, and sends a control signal to a V+ regulator 95 to set an appropriate value for V+. Generally speaking, the algorithm seeks to bring the voltage drops across the active PDACs (Vp) and NDACs (Vn) within appropriate ranges. These ranges are based on the architectures used for the PDACs and NDACs, which as noted earlier comprise current mirrors which use output transistor(s) to drive the currents. As explained in the '181 patent, it is desired that the output transistor(s) operate in a saturation mode, such that the channels of the transistors are in "pinch off." Keeping the output transistor(s) in saturation requires that the drain-to-source voltage drop across the output transistor(s), Vds (i.e., Vp and Vn), be greater that the gate-to-source voltage (Vgs) minus their threshold voltage (Vt). Operation in saturation is desired for providing the proper amount of current: if Vds is too low and the output transistor(s) are operating in sub-saturation, the DACs will not be able to provide the desired current. However, it is also desired that Vds not be too high, because unnecessary additional voltage drop across the output transistor(s) merely wastes power, which is highly undesirable in the battery-operated IPG 100. Due to the differences inherent in the P-channel and N-channel transistors used in the PDACs and NDACs, the desired ranges for Vp and Vn disclosed in the '181 patent are different: e.g., 1.5 to 2.1V for Vp, and 1.2 to 1.8V for Vn. Essentially, the V+ algorithm 90 tries to adjust V+ until Vp and Vn for all the active DACs are within these ranges if possible. (It may not be possible for all of the active DACs to be within these ranges given possible differences in the currents used and difference in tissue resistance between the electrodes).

The V+ algorithm 90 of the '181 patent is described further in FIG. 4. Normally, the algorithm 90 would start with the compliance voltage, V+ at its maximum value (e.g., V+ (max)=18V), and as it operates it gradually reduces V+ to a desired level. The algorithm starts by first acquiring the voltage drops for the active NDACs (Vn1, Vn2, etc.), which measurements are preferably made toward the end of the pulses. Next, a minimum of these voltages (Min(Vn)) is determined. This minimum voltage would suggest the NDAC most at risk to be in sub-saturation, and hence in this embodiment of the algorithm is considered the most efficient to track. Accordingly, the algorithm 90 next asks how that minimum value compares relative to the range of guard band voltages for the NDACs. Essentially, if Min(Vn) is higher than the maximum guard band voltage for the NDACs (e.g., 1.8V), the compliance voltage V+ is decreased, because it can be inferred that all NDACs are at this point operating with voltage drops that are too high to be optimal from a power consumption standpoint. To expedite the iterative nature of the algorithm, the extent to which the compliance voltage V+ is decreased scales with the extent to which Min(Vn) exceeds the upper guard band voltage for the NDACs. Thus, if Min (Vn) is very high above the guard band, the compliance voltage is decreased by a large amount, but if barely above the guard band the compliance voltage is decreased by a small amount.

As the compliance voltage V+ is adjusted, Min(Vn) will eventually come within the guard band range (e.g., between 1.2V and 1.8V), and the PDACs can then be assessed. The algorithm 90 then measures the voltage drops for the active PDACs (Vp1, Vp2, etc.). Next, a minimum of these voltages (Min(Vp)) is determined, and the algorithm 90 then proceeds as described earlier for the NDACs by adjusting V+ until the Min(Vp) brought within its guard band range (e.g., between 1.5V and 2.1V). At this point, V+ is now set for the IPG at value V+(opt).

FIG. 5 further illustrates the operation of V+ algorithm 90, and assumes for simplicity that only one PDAC and one NDAC are operating to provide constant current pulses at electrodes E1 and E2, and thus each measured Vn or Vp comprises the minimum for purposes of the algorithm 90. As shown, the compliance voltage V+ starts at a maximum value (V+(max)). Then Vn is measured at the end of the pulse across the active NDAC that is sinking current from electrode E2. If Vn is higher than its guard band range, the V+ algorithm reduces V+, and Vn is then measured on a subsequent pulse. Eventually as V+ falls, Vn is brought within its guard band, and the V+ algorithm 90 can start monitoring Vp at the end of the pulses for the active PDAC that is sourcing current to electrode E1. If Vp is higher than its guard band range, the V+ algorithm reduces V+, and Vp is again measured on a subsequent pulse. Eventually Vp is brought within its guard band, at which point V+ determines that the current value for V+ is optimal, and thus V+ is set by algorithm 90 to that optimal value, V+(opt).

BRIEF DESCRIPTION OF THE DRAWINGS

FIG. 12B illustrates details of the voltage selection circuitry of the circuit of FIG. 12A, in accordance with an embodiment of the present invention.

DETAILED DESCRIPTION

Figure 6A:
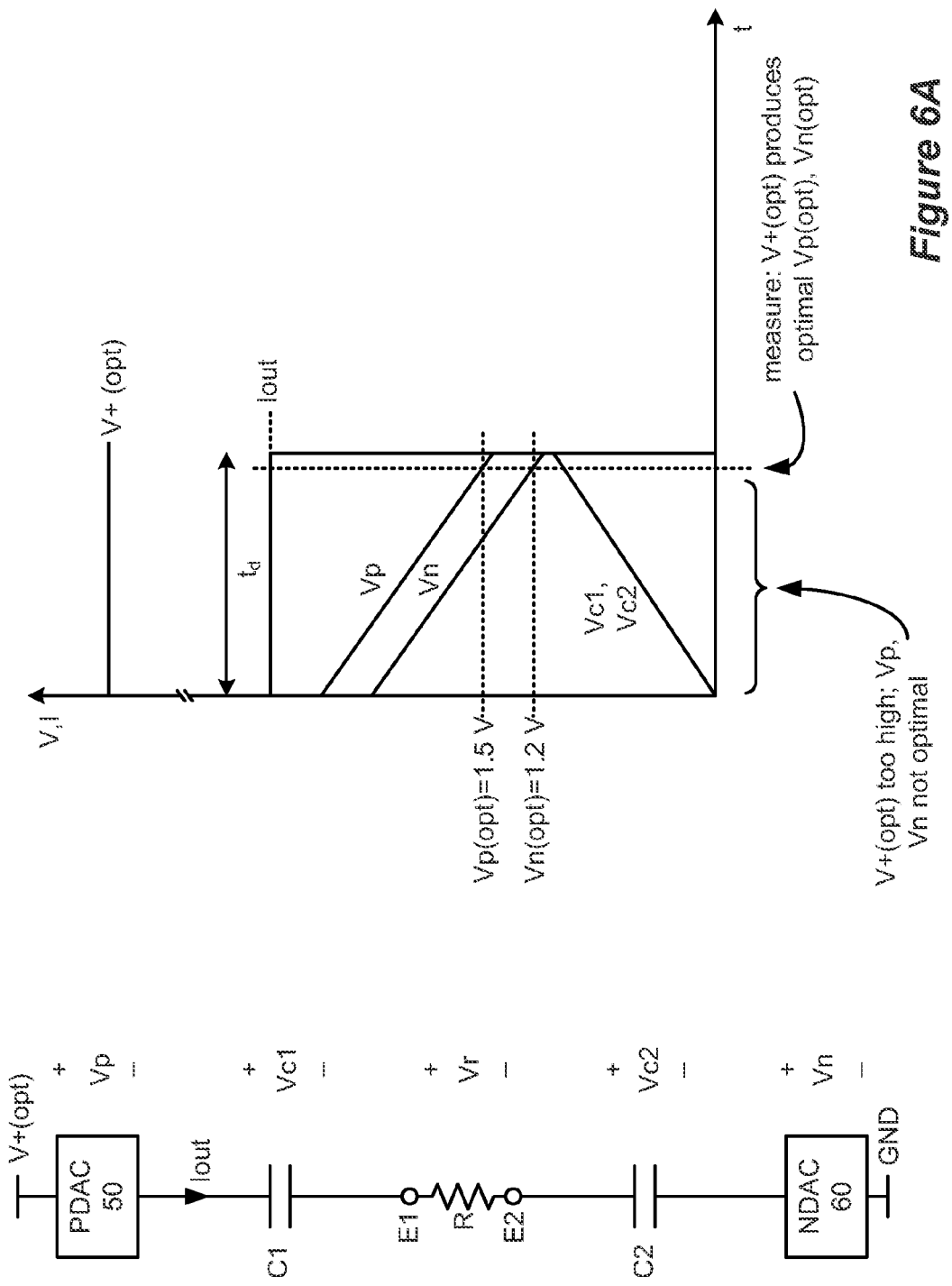
FIGS. 6A-6B illustrate power wastage in the setting of compliance voltage by the compliance voltage algorithm of FIG. 4 for uniphasic and biphasic current pulses.

FIG. 6A shows the passage of a current pulse from electrode E1 to electrode E2 as described earlier, and the circuitry involved, including (in this example) one PDAC 50, the decoupling capacitor connected to E1, the patient's tissue R, the decoupling capacitor connected to E2, and one NDAC 60. Each of these serially-connected circuit elements will drop some portion of the compliance voltage V+, i.e., V+=Vp+Vc1+Vr+Vc2+Vn. The voltage drop through the tissue, Vr, is difficult to know a priori, but in any event will remaining constant over the duration of the pulse. By contrast, the voltage drop across the decoupling capacitors C1 and C2, Vc1 and Vc2, will increase as current is injected through them. If the capacitances C1 and C2 are the same, the slope of the increase of Vc1 and Vc2 during the pulse would be the same as shown.

If V+ is set to a constant value, V+(opt), then because Vr is constant, and because Vc1 and Vc2 increase, the voltage drops across the PDAC 50 and NDAC 60, Vp and Vn, will necessarily decrease according to the equation set forth above. Measuring Vp and Vn near the end of the pulse only sets V+ to the optimal value V+(opt) at that point in time, for it is only at this time that Vp=Vp(opt) (e.g., 1.5V) and Vn=Vn(opt) (e.g., 1.2V). Said differently, the output transistor(s) in the DACs are only at an optimal saturation point (not too high or low) at this point in time. This means that V+(opt) is not actually optimal earlier in the pulse. At the beginning of the pulses, V+(opt), and therefore Vp and Vn, are too high, which wastes power.

Figure 6B:
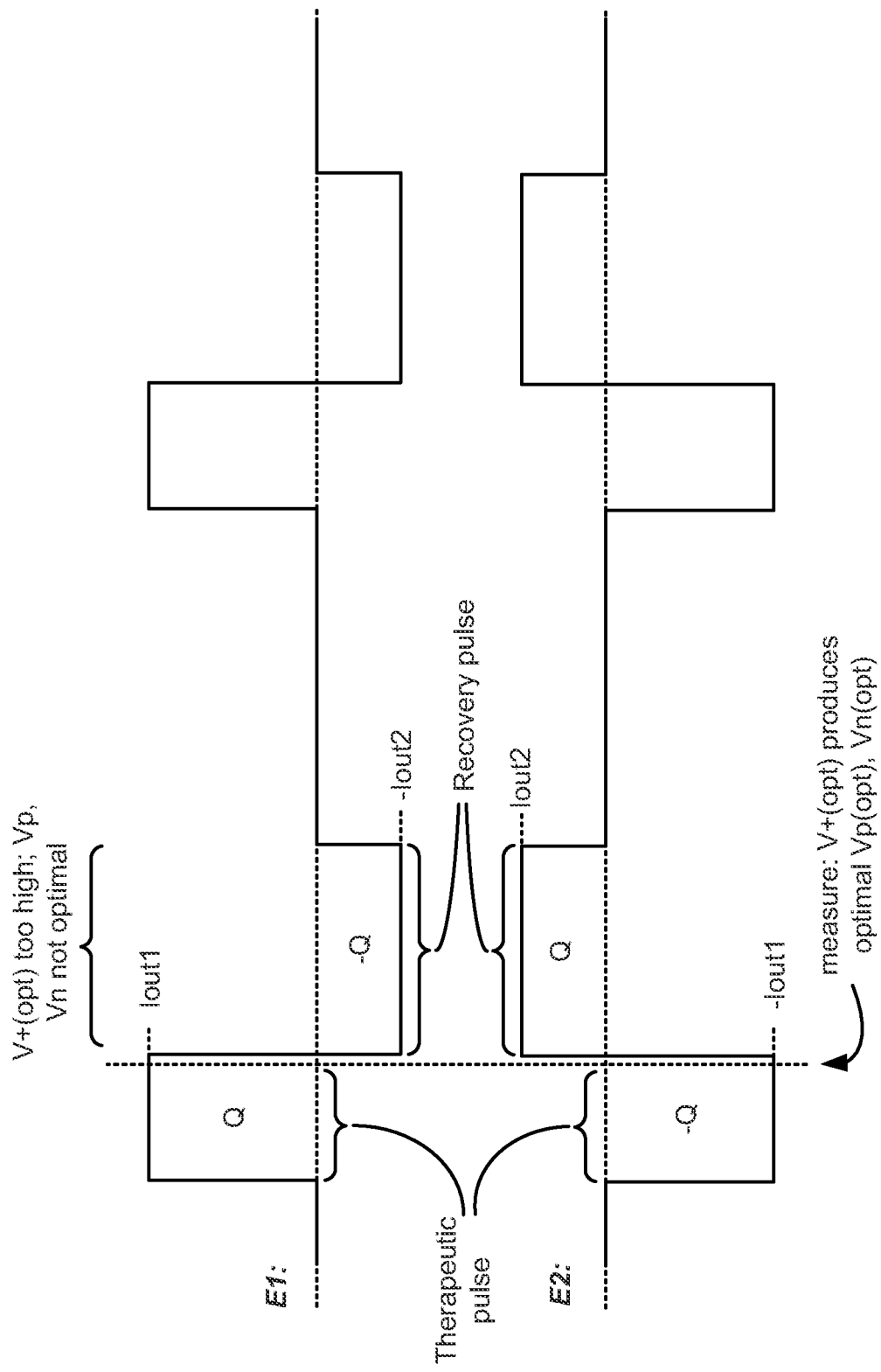

FIG. 6B illustrates another inefficiency resulting from the use of biphasic pulses, i.e., pulses which have two phases. The two phases illustrated comprise a therapeutic pulse phase of magnitude Iout1, followed by a recovery pulse phase of lower magnitude Iout2 and of opposite polarity. The recovery pulse is generally not mandated by patient therapy, but is instead used to remove charge that accumulated on the decoupling capacitors during the larger-magnitude therapeutic pulse. As just noted, the decoupling capacitors will store charge as current passes through them, which is generally undesired. Reversing the current through those capacitances during the recovery pulse seeks to actively recover such stored charge. To actively recover stored change in this fashion, it is preferable that the same amount of charge (Q) be passed in the recovery pulse as was passed in the therapeutic pulse. While this can be done by making the amplitude and pulse width of the recovery pulse equal to that of the therapeutic pulse, it is more common to make the recovery pulse of longer duration and lower amplitude so that it has less effect on the patient.

Figure 1A:
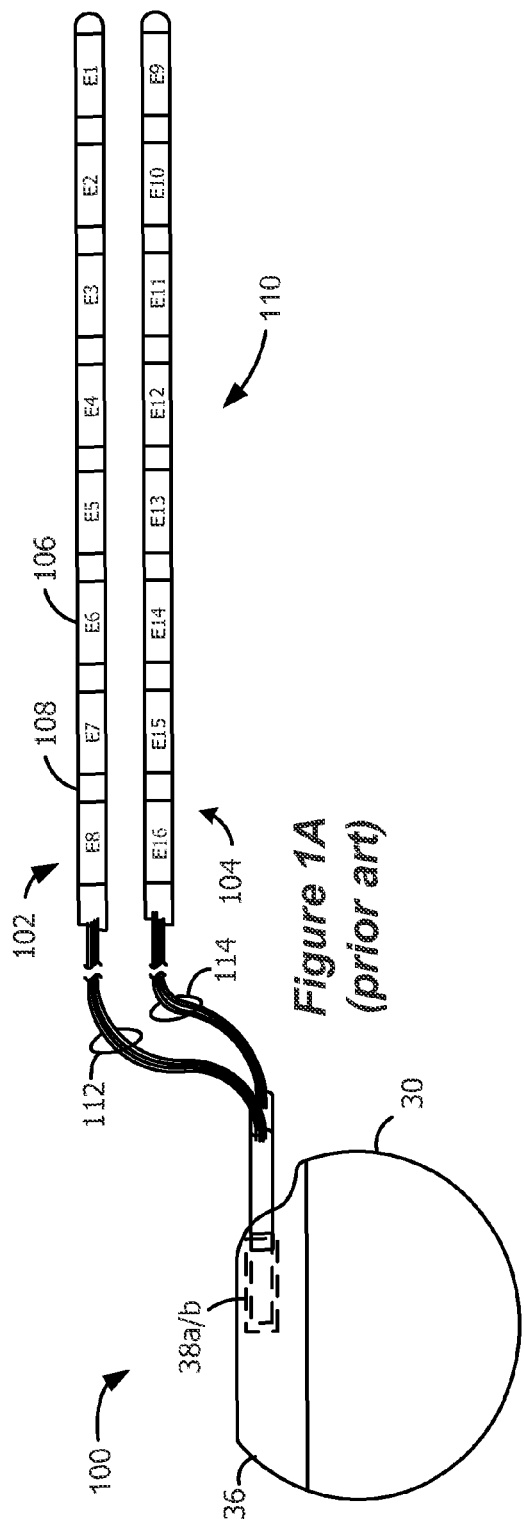
FIGS. 1A-1C illustrate different views of an implantable medical device, specifically an Implantable Pulse Generator (IPG).
Figure 1C:
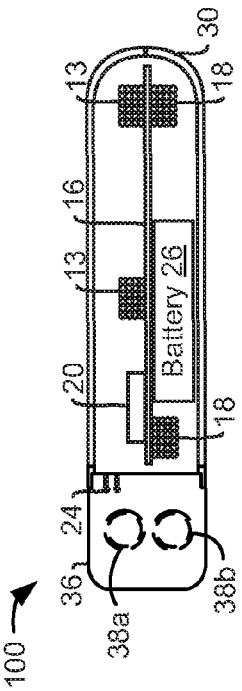
Figure 1B:
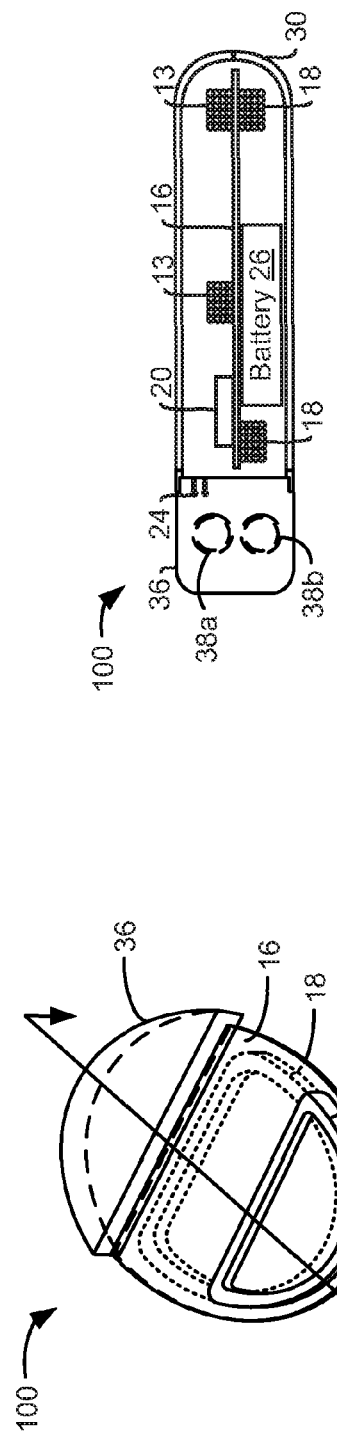
Figure 2B:
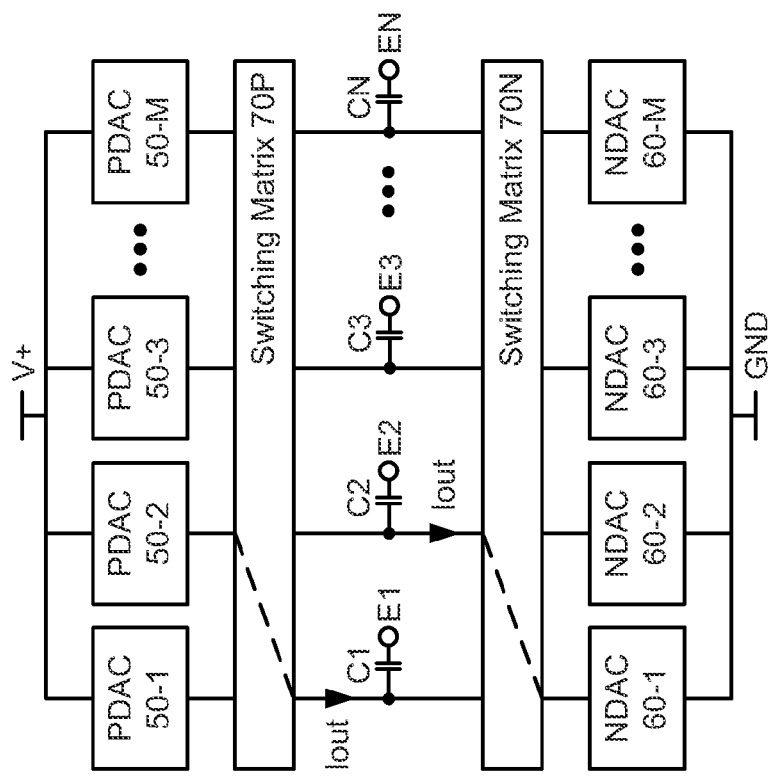
FIGS. 2A-2B illustrate various current distribution architectures for forming pulses at electrodes of the IPG.
Figure 2A:
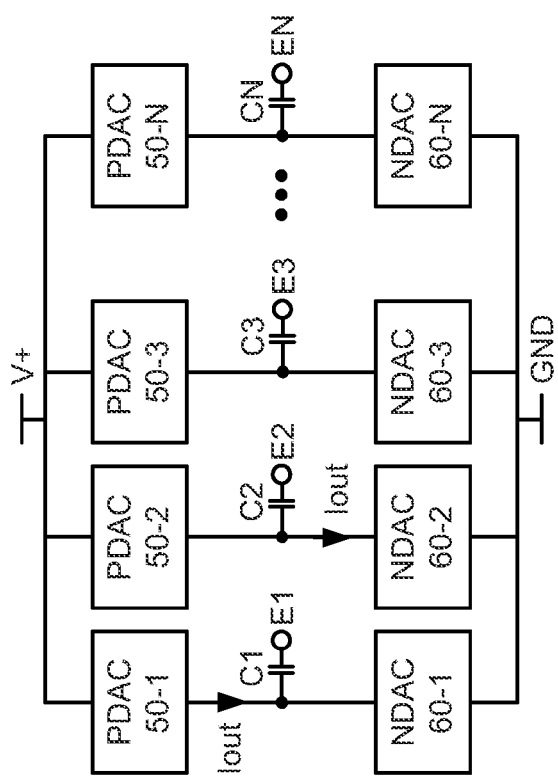
Figure 3:
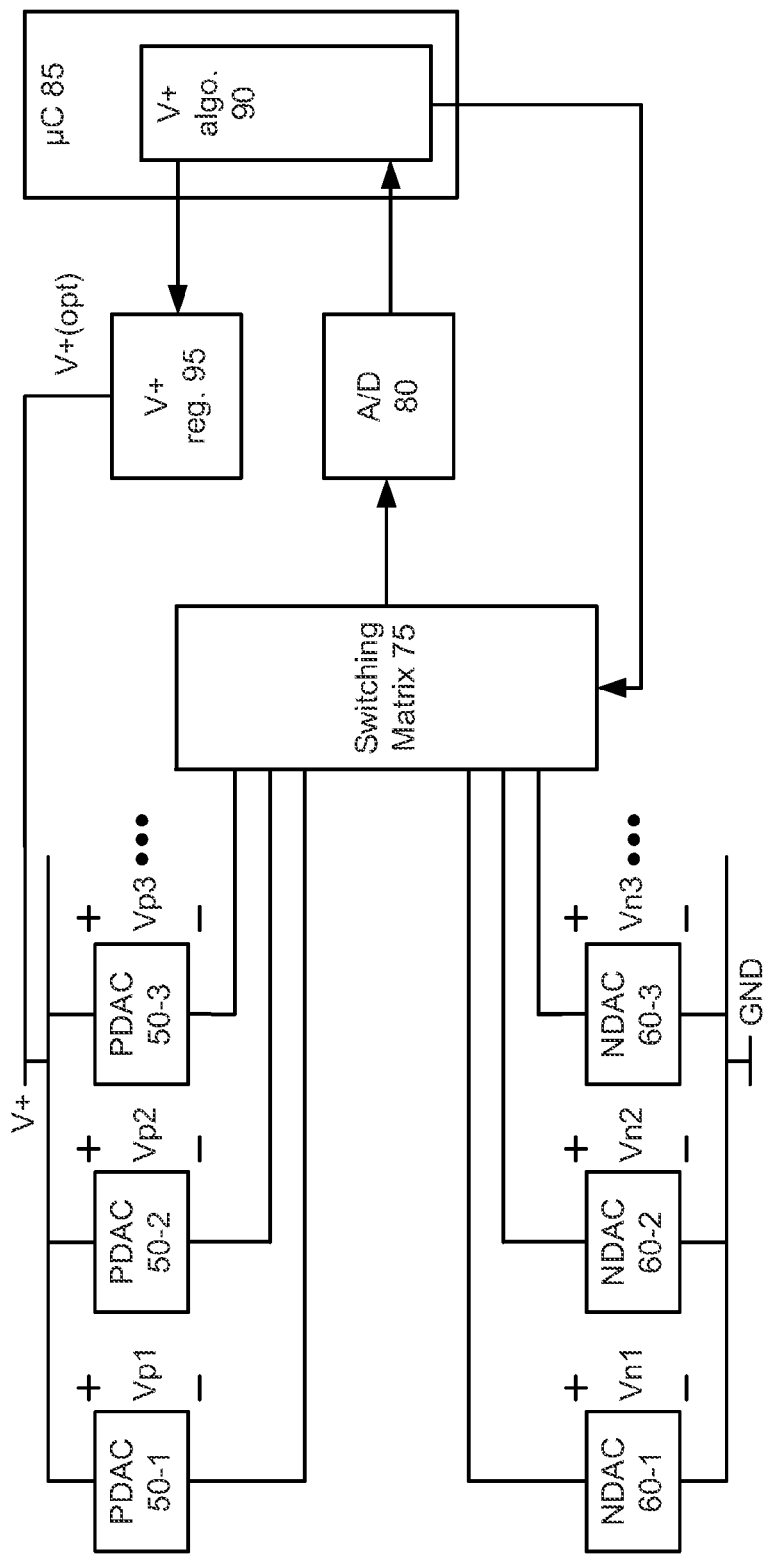
FIG. 3 illustrates a block diagram for circuitry used to set a compliance voltage of the IPG in the prior art.
Figure 4:
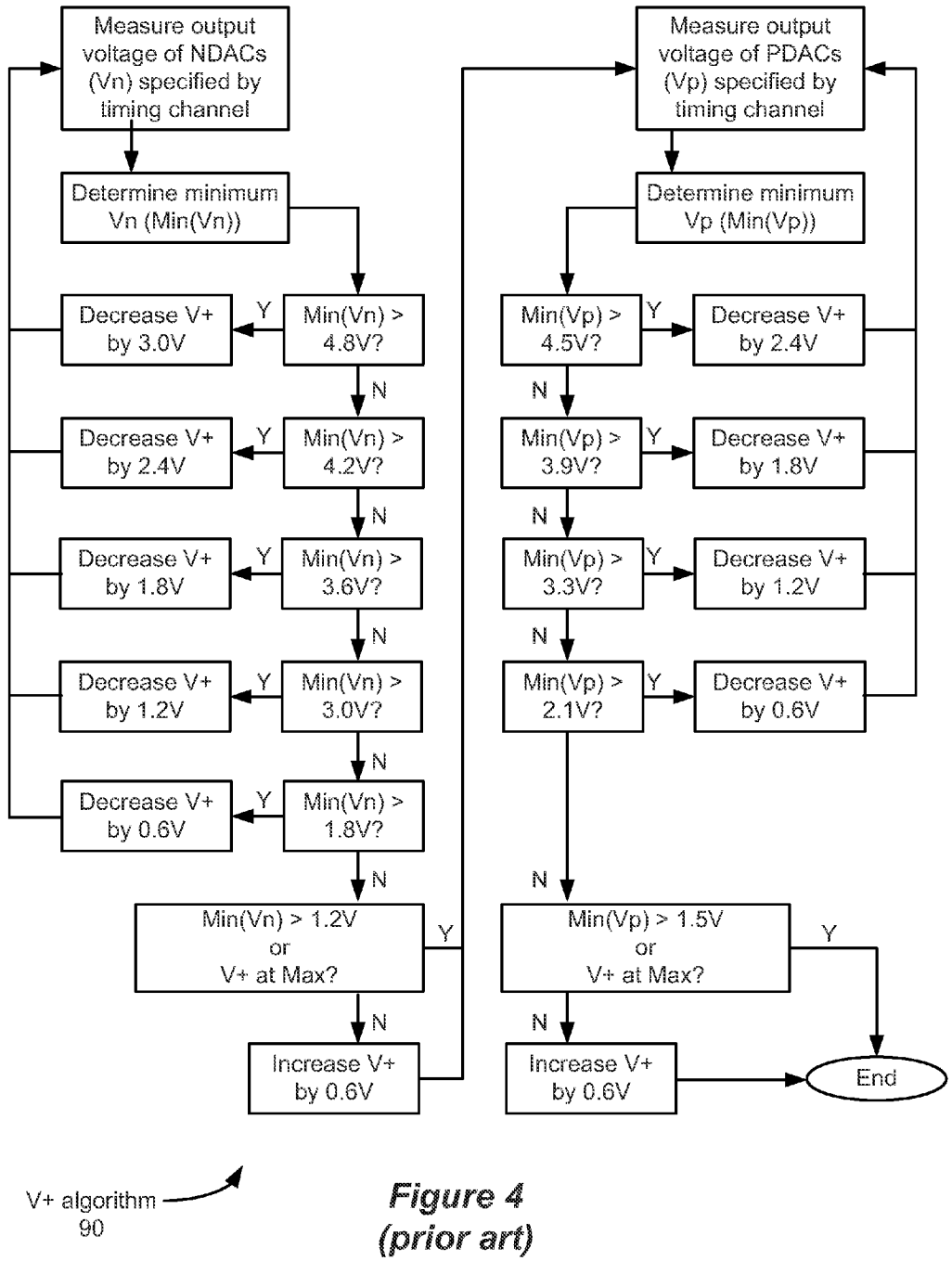
FIG. 4 illustrates a flowchart illustrating the compliance voltage algorithm for setting the compliance voltage of the IPG in the prior art.
Figure 5:
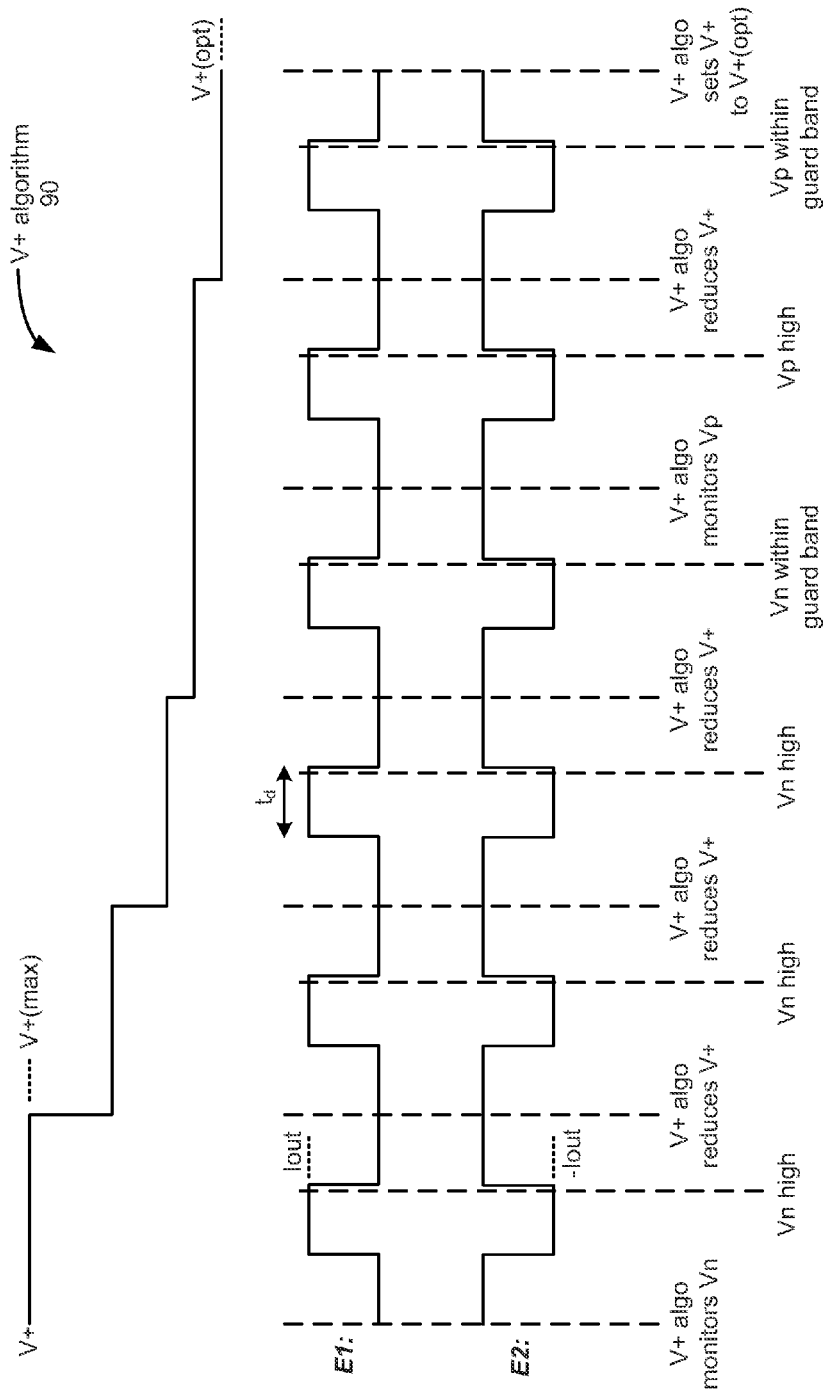
FIG. 5 illustrates waveforms illustrating the setting of compliance voltage by the compliance voltage algorithm of FIG. 4 in the prior art.

Just like the therapeutic pulses, the recovery pulses must be generated by a PDAC and NDAC. (If a dedicated architecture is used as in FIG. 2A, the other of the dedicated PDAC or NDAC for the active electrodes would be used during the recovery phase; if a distributed architecture is used as in FIG. 2B, the same PDACs and NDACs can be used, with the switching matrices 70P and 70N now coupling them to the other electrode during the recovery phase). But as just noted, the recovery pulses will likely be of lower magnitude than the active pulses. If V+(opt) is set at a single point in time during higher-magnitude therapeutic pulses, V+(opt), and Vp and Vn, are will be too high and therefore inefficient during the lower-magnitude recovery pulses.

Additionally, as the IPG continues to operate, there can be changes that might require resetting V+(opt). For example, the electrodes may shift in the patient as the patient moves. Such movement can change the resistance R of the tissue through which the pulses flow, and thus change the voltage drop, Vr, across the tissue. Because V+ is a function of Vr, such changes in Vr could suggest that V+(opt) should also be changed.

The inventors disclose improved circuitry for generating a compliance voltage (V+) for the current sources and/or sinks in an implantable stimulator device, which alleviates the foregoing concerns. The improved V+ generation circuitry adjusts V+ to an optimal value in real time, even during the provision of a stimulation current. The circuitry uses amplifiers to measure the voltage drop across an active PDACs (current sources) and/or NDAC (current sinks) in real time during the provision of the stimulation current. The measured voltages are input to a V+ regulator, which compares the measured voltage drops across the DACs to optimal values, and which feeds an optimized value for V+ back to the DACs in real time to keep the voltage drop(s) at those optimal levels for efficient DAC operation.

Figure 7:
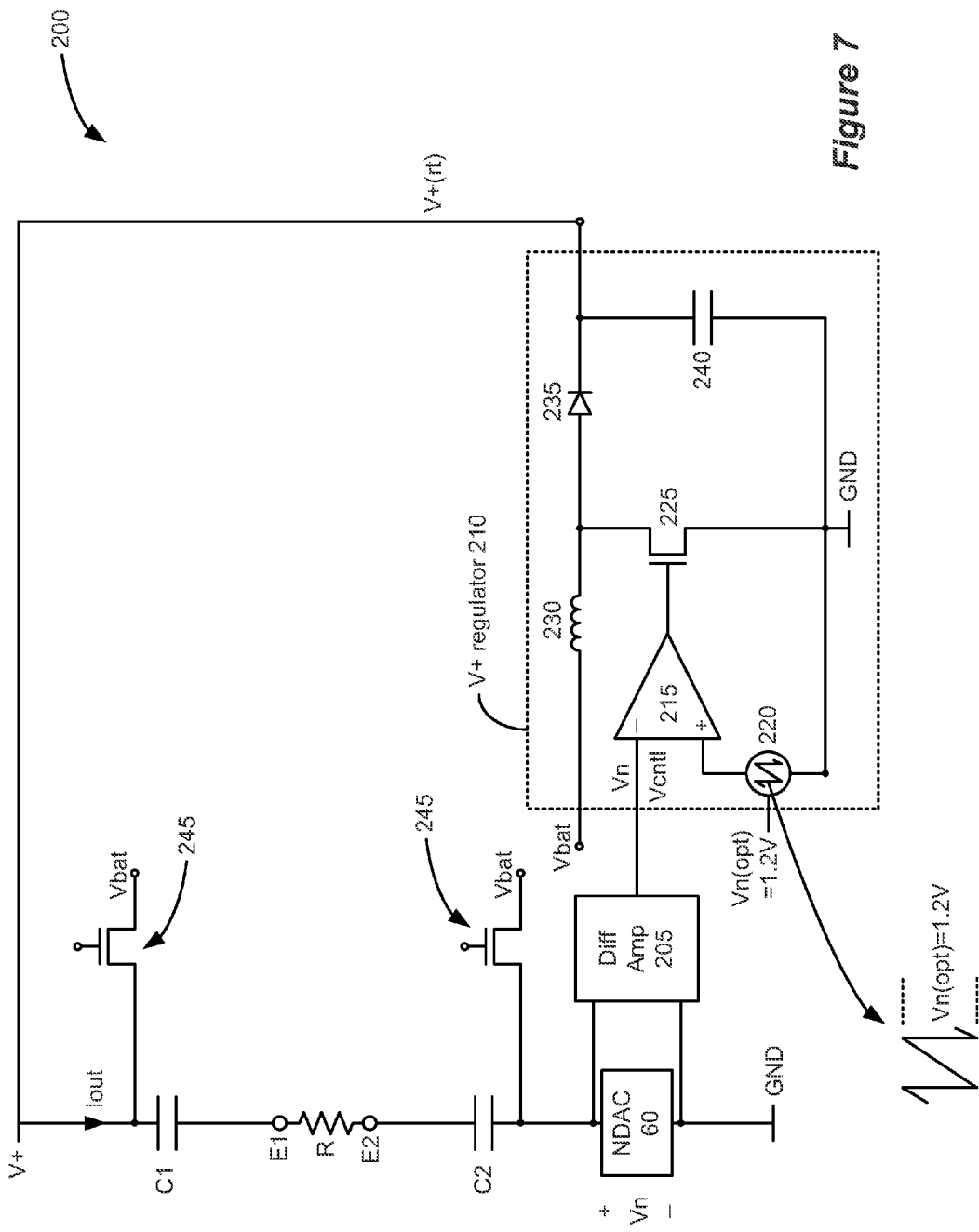
FIG. 7 illustrates an improved compliance voltage generation circuit used with architectures having a single current generator, in accordance with an embodiment of the present invention.

A first example of improved V+ generation circuitry 200 is shown in FIG. 7. In this first example, only a single current generator is used to provide the desired current, Iout, from electrode E1 to electrode E2. In the illustrated example, this single current generator comprises a current sink, namely NDAC 60, and the source for the current comprises the compliance voltage, V+, which in this example comprises a passive source. Although not shown, the single current generator could also comprise a current source (e.g., a PDAC 50), with ground operating as a passive sink.

A differential amplifier 205 measures the voltage drop, Vn, across the NDAC 60, and this value is input to a V+ regulator 210. V+ regulator 210 in this example comprises a boost converter modified as described below to allow for faster operation and able to adjust V+ in real time (V+(rt)). The V+ regulator 210 generates V+(rt) from the battery in the IPG, i.e., from Vbat. The V+ regulator 210 comprises a comparator 215 for receiving Vn at its inverting terminal, and receives a sawtooth voltage from a sawtooth generator 220 at its non-inverting terminal. The sawtooth voltage has a maximum value, Vn(opt), which is tunable to set the desired voltage drop across the NDAC 60 for efficient operation. As noted earlier, Vn(opt) can be 1.2V, which voltage can be generated using a tunable bandgap reference voltage generator for example (not shown). The output of comparator 215 is sent to the gate of a pulse width modulation (PWM) transistor 225. The output of the comparator 215 turns on the PWM transistor 225 when the magnitude of the sawtooth exceeds Vn. When this occurs, an inductor 230 is shorted to ground, and draws current. When the sawtooth wave returns to zero, Vn will be higher, and the comparator 215 will turn off the transistor 225, causing the inductor 230 to inject its stored current through a diode 235 to a storage capacitor 240 where the compliance voltage V+(rt) is formed. V+(rt) is then feed back to the current distribution circuitry to provide power to drive the stimulation current as shown.

Thus, when Vn falls below the desired value of Vn(opt)=1.2V, the PWM transistor 225 will be on for some duty cycle relative to the frequency of the sawtooth wave, with lower Vn values establishing longer duty cycles. Duty cycling the PWM transistor will increase V+(rt), thereby increasing Vn via the feedback loop. If Vn is greater than Vn(opt)=1.2V, the PWM transistor 225 will be off, the inductor 230 will not receive current, and V+(rt) and Vn will begin to fall. In short, V+ regulator 210 works to keep Vn at it optimal vale of Vn(opt)=1.2V.

As mentioned earlier, the V+ regulator 210 is modified to adjust V+ in real time. Normally, the storage capacitor 240 on a boost converter is relatively large (e.g., 28 µF) to hold and filter the generated voltage. In V+ regulator 210, the storage capacitor 240 is significantly smaller (e.g., 7.5 nF), which allows V+(rt) to change much more rapidly in real time, even during the provision of the current pulse. Rapid response in adjusting V+(rt) is further assisted by increasing the frequency of the sawtooth generator (e.g., to 1 MHz), and by lowering the inductance of the inductor (e.g., to 5 pH). Such values for the components in V+ regulator 210 allow V+(rt) to change suitably quickly relative to the time scale of the pulses that the current distribution circuitry creates. Routine experimentation and simulation of these values can further improve V+(rt) response if necessary.

The V+ regulator 210 need not comprise a boost converter, and can comprise any kind of efficient voltage converter, such as those employing switches capacitor, and can regulate V+(rt) in light of voltage drop across the DAC(s) in other ways. Thus, the use of a sawtooth generator 220 controlling a PWM transistor 225 is merely one example of such regulation.

Figure 8:
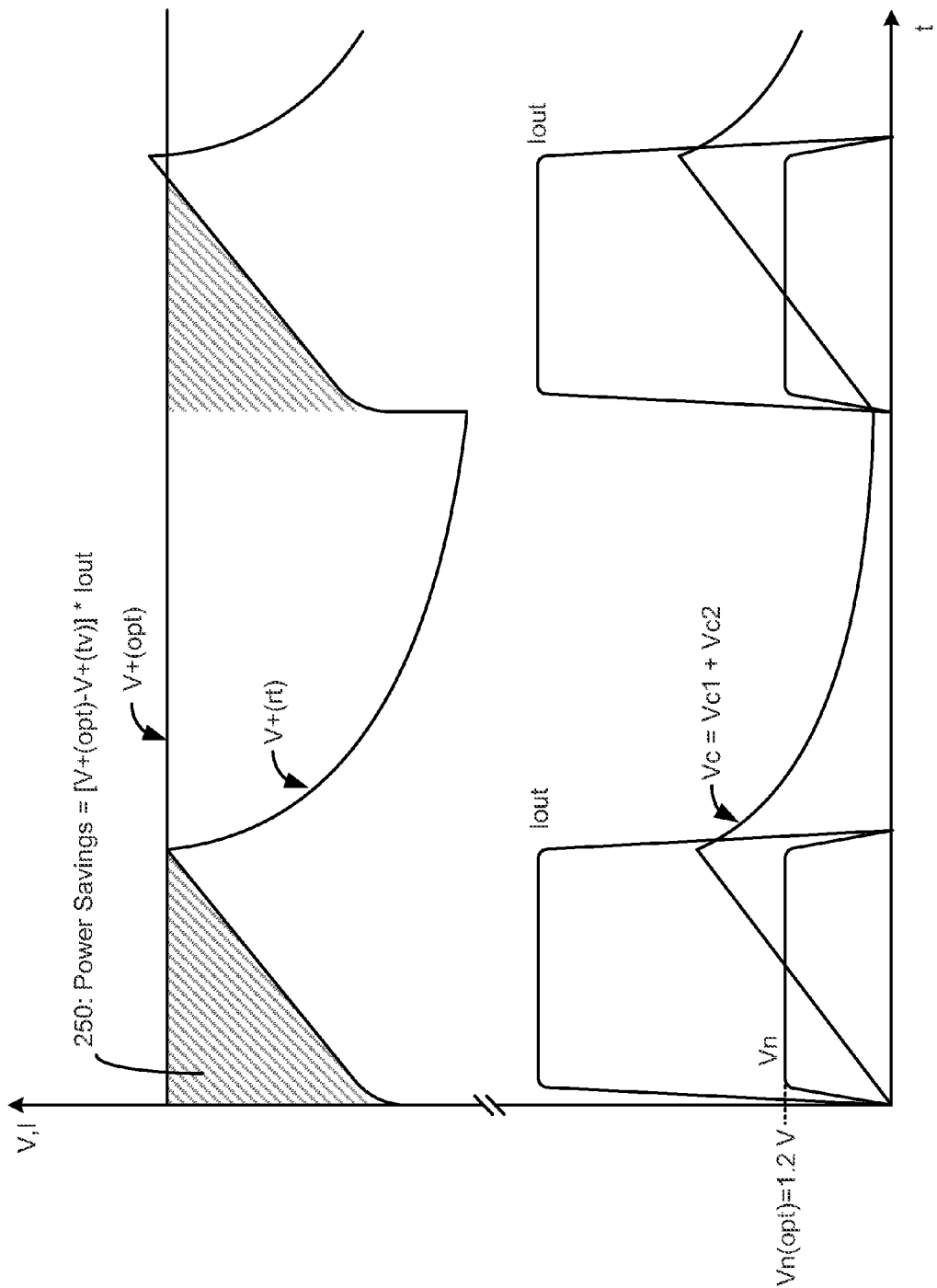
FIG. 8 illustrates waveforms of various voltages generated during the operation of the improved compliance voltage generation circuit of FIG. 7 during uniphasic current pulses, in accordance with an embodiment of the present invention.

FIG. 8 shows the various voltages that are created as the V+ generation circuitry 200 of FIG. 7 operates to create a uniphasic pulse. When NDAC 60 is initially programmed to provide Iout, V+(rt) is at an indeterminate value, but nonetheless quickly ramps up to an appropriate value by virtue of fast-acting V+ regulator 210 to establish the appropriate voltage drop across the NDAC 50, Vn(opt)=1.2V. During this short ramp-up period, Iout also ramps, but this small deviation from an otherwise ideal square wave is not clinically significant. What the appropriate value of V+(rt) will be may not be known a priori as the tissue resistance is not necessarily known or stable, as mentioned earlier. Nonetheless, as Iout flows, the decoupling capacitors C1 and C2 begin to charge, and the voltage across them increases. These voltages are summed (Vc=Vc1+Vc2) in FIG. 8. The feedback loop established by the V+ regulator 210 begins to compensate for this increase in voltage, and V+(rt) increases with the same slope as Vc. Meanwhile, and significantly, Vn has stayed at its ideal value of Vn(opt)=1.2V throughout the pulse.

Keeping Vn at its ideal value for efficient operation of the NDAC 60 results in power savings, and that savings can be seen in the shaded triangular region 250, which reflects the difference between a constant V+(opt) and V+(rt) as generated by the improved V+ generation circuitry 200.

After the pulse, the V+ regulator 210 can be disabled (e.g., by disconnecting the battery), and V+(rt) will fall as shown. The rate of decline will be governed by the storage capacitor 240 in the V+ regulator 210 and other resistances inherent in the system. During this interpulse period, attempts are also made to recover the charge that has been stored on the decoupling capacitors C1 and C2, and thus their summed voltage Vc will also fall as shown. Charge recovery in this example occurs passively, through the use of passive recovery switches 245, shown in FIG. 7. Such switches 245 are connected to each of the decoupling capacitors C1-CN. In this passive charge recovery phase, the decoupling capacitors C1-C2 are shorted to a common potential via the switches 245. The common potential illustrated is Vbat, the voltage of the battery, although other reference potentials could be used as well. Shorting the capacitors to Vbat effectively shorts them through the patient's tissue, and thus equilibrates any stored charge to assist in charge recovery. Some current distribution architectures may short only the previously-active electrodes by closing only the passive recovery switches 245 coupled to those electrodes, while other architectures will short all of the electrodes (even those that were not previously active) by closing all of the passive recovery switches 245.

Returning to FIG. 8, the V+ regulator 210 can be enabled at the beginning of a next pulse (e.g., by reconnecting the battery). At the beginning of the next pulse it is seen that V+(rt) has fallen to an indeterminate value. However, any existing potential of V+(rt) is beneficial to assisting the V+ regulator 210 to more quickly establish an appropriate V+(rt) value for the next pulse. If passive charge recovery from the decoupling capacitors C1 and C2 has not been perfect, Vc will not be zero at the beginning of the next pulse. Thus, Vc will be slightly increased as compared to the first pulse, and V+(rt), to compensate, will be higher as well. Nonetheless, Vn still stays at its optimal value of Vn(opt)=1.2V by virtue of the V+ regulator 210 feedback loop.

Figure 9:
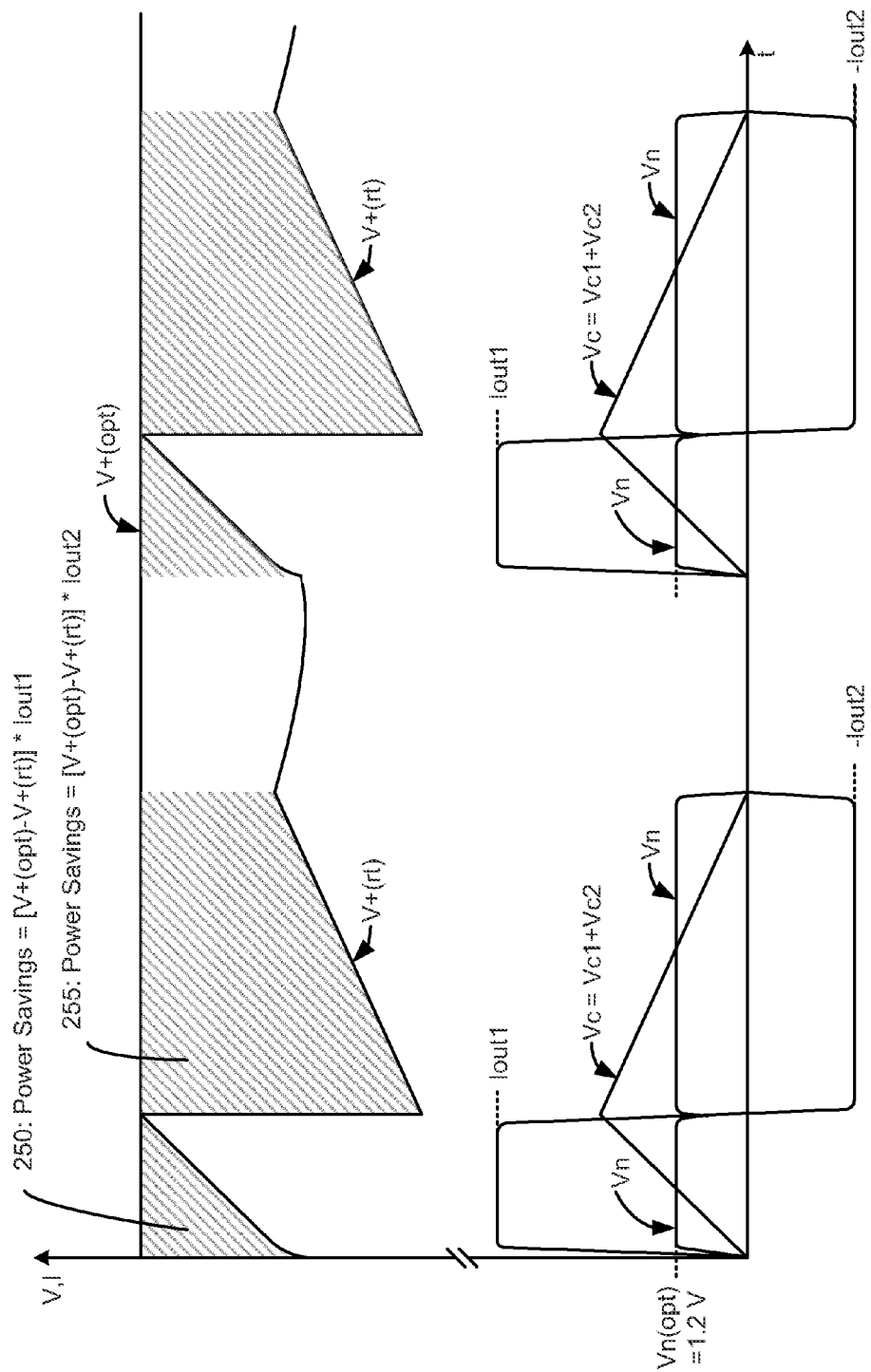
FIG. 9 illustrates waveforms of various voltages generated during the operation of the improved compliance voltage generation circuit of FIG. 7 during biphasic current pulses, in accordance with an embodiment of the present invention.

FIG. 9 shows the various voltages that are created as the V+ generation circuitry 200 of FIG. 7 operates to create a biphasic pulse, as was illustrated in FIG. 6B earlier. The first, high-amplitude (Iout1) therapeutic pulse operates the same as was just described in FIG. 8 for a uniphase pulse, and thus is not further explained. During the recovery phase, a longer duration, lower amplitude pulse (Iout2) of opposite polarity is called for, as described earlier. The compliance voltage need not be as high to generate this lower amplitude recovery pulse, and so it is seen that V+(rt) drops at the beginning of the recovery pulse to once again keep Vn at Vn(opt)=1.2V. The extent of this drop will depend in part on the relative magnitudes of Iout1 and Iout2.

The purpose of the recovery phase, as noted earlier, is to recover the charge stored on the capacitors during the therapeutic pulse, and it is seen that voltage drop across the capacitors C1 and C2 (Vc) drops to zero at the end of the recovery pulse. Because the current has reversed polarity in the recovery pulse, the voltages stored on the capacitors are of reversed polarity compared to V+ in this phase as well. Thus, discharging the capacitors requires V+(rt) to increase over the duration of the recovery pulse as shown to compensate, and to keep Vn at Vn(opt)=1.2V. After the recovery pulse, passive recovery using switches 245 (FIG. 7) can begin if necessary, and V+ will again begin to fall to an indeterminate state at the beginning of the next pulse.

Lowering V+(rt) during the recovery pulse while keeping Vn at its ideal value for efficient operation of the NDAC 60 results in even further power savings, and such additional savings can be seen in the shaded region 255, which reflects the difference between a constant V+(opt) and V+(rt) as generated by the improved V+ generation circuitry 200.

Figure 10A:
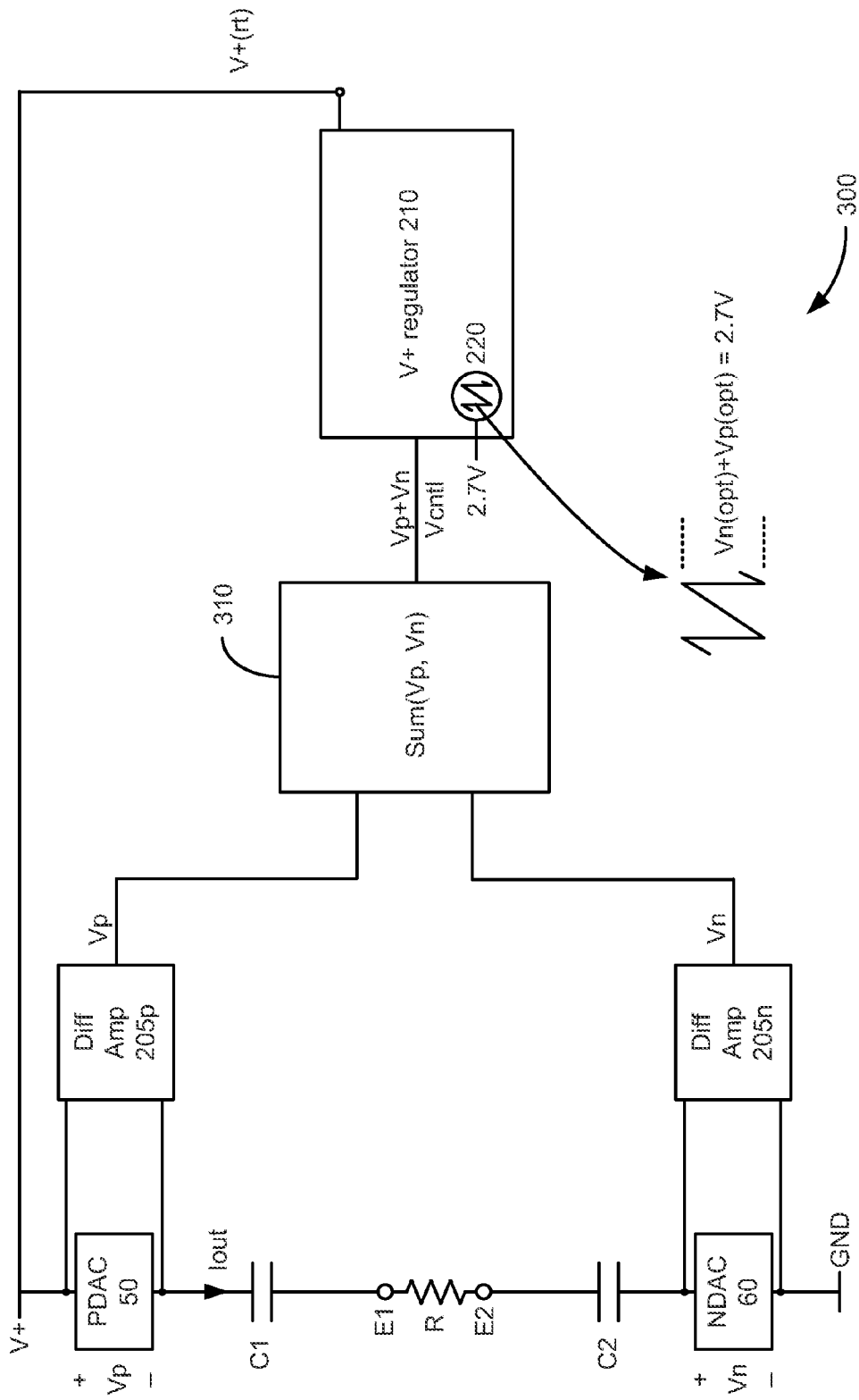
FIG. 10A illustrates the improved compliance voltage generation circuit used in architectures employing a current source and a current sink, and illustrates the compliance voltage being set as a function of the sum of the required optimum voltages for the current source and sink, in accordance with an embodiment of the present invention.

FIG. 10A shows an extension of the disclosed concept to current distribution architectures employing two current generators to provide the desired current, Iout, from electrode E1 to electrode E2. A PDAC 50 is used to source the current to E1 and an NDAC 60 is used to sink current from E2. In this version of the improved V+ generation circuitry 300, both of the voltage drops across the PDAC 50 and the NDAC 60, Vp and Vn, are monitored in real time, and are used to produce a real time varying compliance voltage V+(rt) that optimally biases both current generators for efficient operation. In this example, V+(rt) is established by ensuring that the summed voltage drops Vp and Vn are equal to summed optimal voltages for these parameters. In other words, V+(rt) is set in real time so that Vp+Vn=Vp(opt)+Vn(opt). Assuming Vp(opt)= 1.5V and Vn(opt)=1.2V, then V+ generation circuitry sets V+(rt) so that Vp+Vn=2.7V.

Figure 10B:
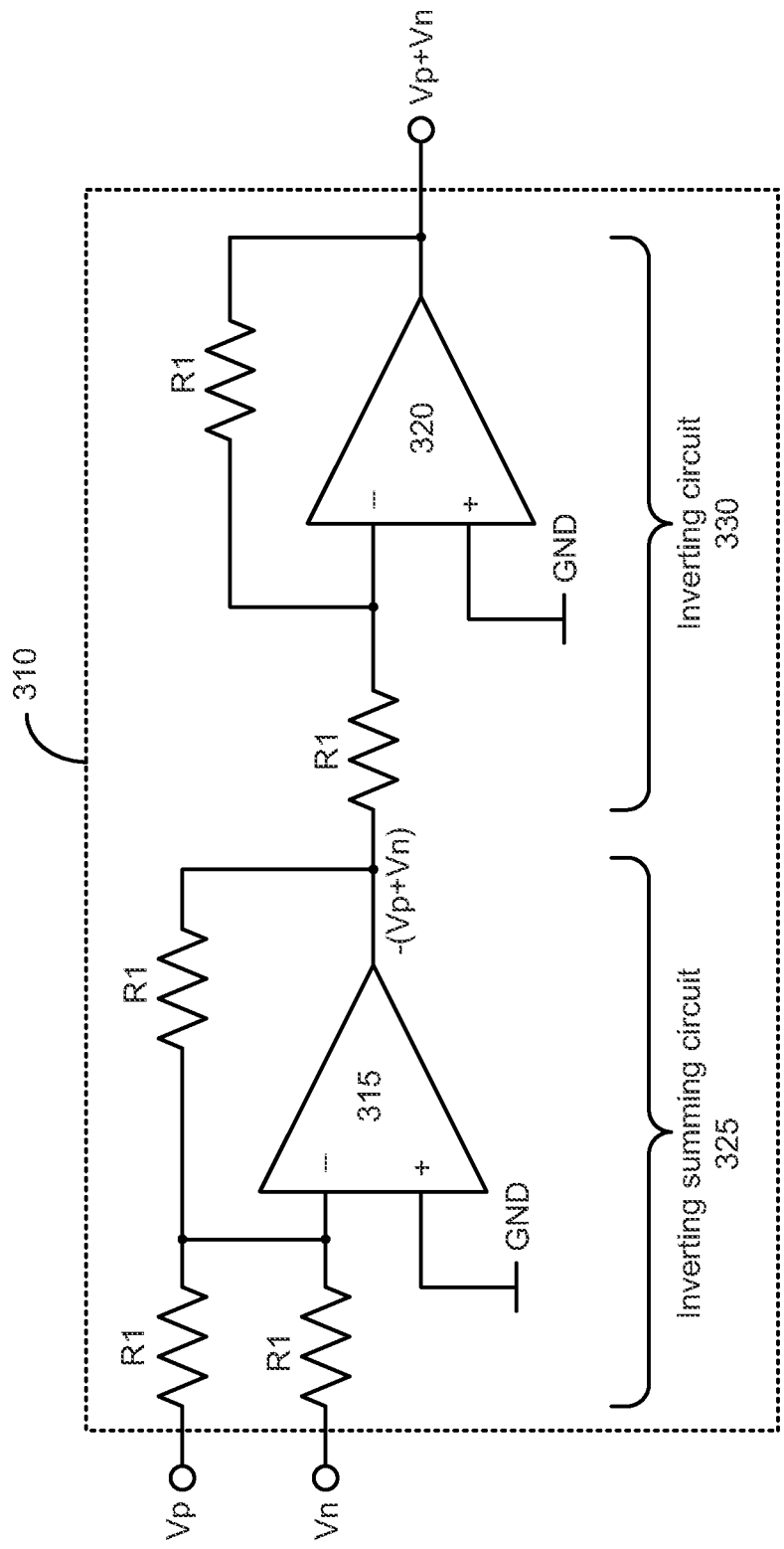
FIG. 10B illustrates a circuit diagram for the summing circuit of FIG. 10A, in accordance with an embodiment of the present invention.

Vp and Vn are measured by differential amplifiers 205p and 205n respectively, and those values are sent to an analog summing circuit 310, which is shown in detail in FIG. 10B. Analog summing circuit 310 comprises an inverting summing circuit 325, which uses an operational amplifier 315 and a resistive network to produce the inverse of the sum (−(Vp+Vn)). Inverting summing circuits 325 are well known and are not further explained. This inverted sum is then input to an inverting circuit 330. The inverting circuit 330 also comprises an operational amplifier 320 and a resistive network, and operates to invert the input to produce the desired sum Vp+Vn. Again, inverting circuits 330 are well known and are not further explained.

Returning to FIG. 10A, the sum of Vp and Vn is input to the V+ regulator 210, which can be similar to that described earlier with reference to FIG. 7. One important difference however is tuning the maximum value of the sawtooth voltage produced by the sawtooth generator 220. In this instance, the sawtooth voltage is tuned to a maximum value of Vn(opt)+Vp(opt), or 2.7V, which one will understand from earlier discussion will result in establishing Vn+Vp=2.7V across the PDAC 50 and NDAC 60. As noted earlier, Vn(opt)=1.2V, Vp(opt)=1.5V, or their sum, can be generated using tunable bandgap reference voltage generators (not shown).

Figure 11:
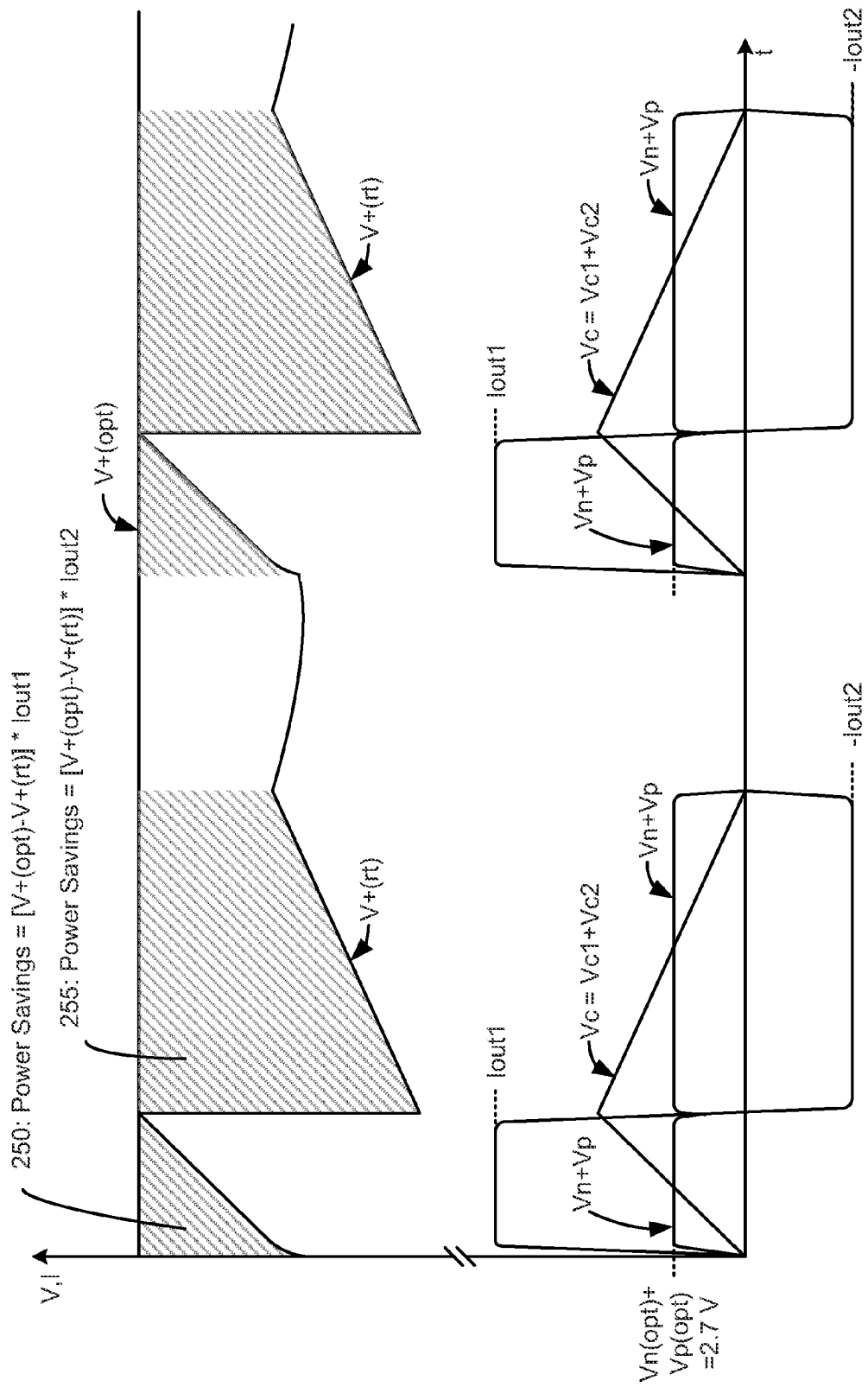
FIG. 11 illustrates waveforms of various voltages generated during the operation of the circuit of FIG. 10A during biphasic current pulses, in accordance with an embodiment of the present invention.

FIG. 11 shows the various voltages that are created by the V+ generation circuitry 300 of FIG. 10A when powering a biphasic pulse. FIG. 11 is essentially the same as shown in FIG. 9, and is therefore not again discussed, other than to note that Vn+Vp is efficiently held constant at 2.7V. Note that in this example circuit 300, it is not known how Vp or Vn might be individually varying. Thus, for example, the NDAC 60 may be "weak," such that Vn is actually below its optimal value of Vn(opt)=1.2V, while PDAC 50 may be "strong," such that Vp is actually above its optimal value of Vp(opt)=1.5V. Even if one of Vp or Vn is not optimal, optimizing their sum by adjusting V+(rt) in real time will still generally allow for proper delivery of the stimulation currents given the serial connection between the PDAC 50 and the NDAC 60.

Figure 12A:
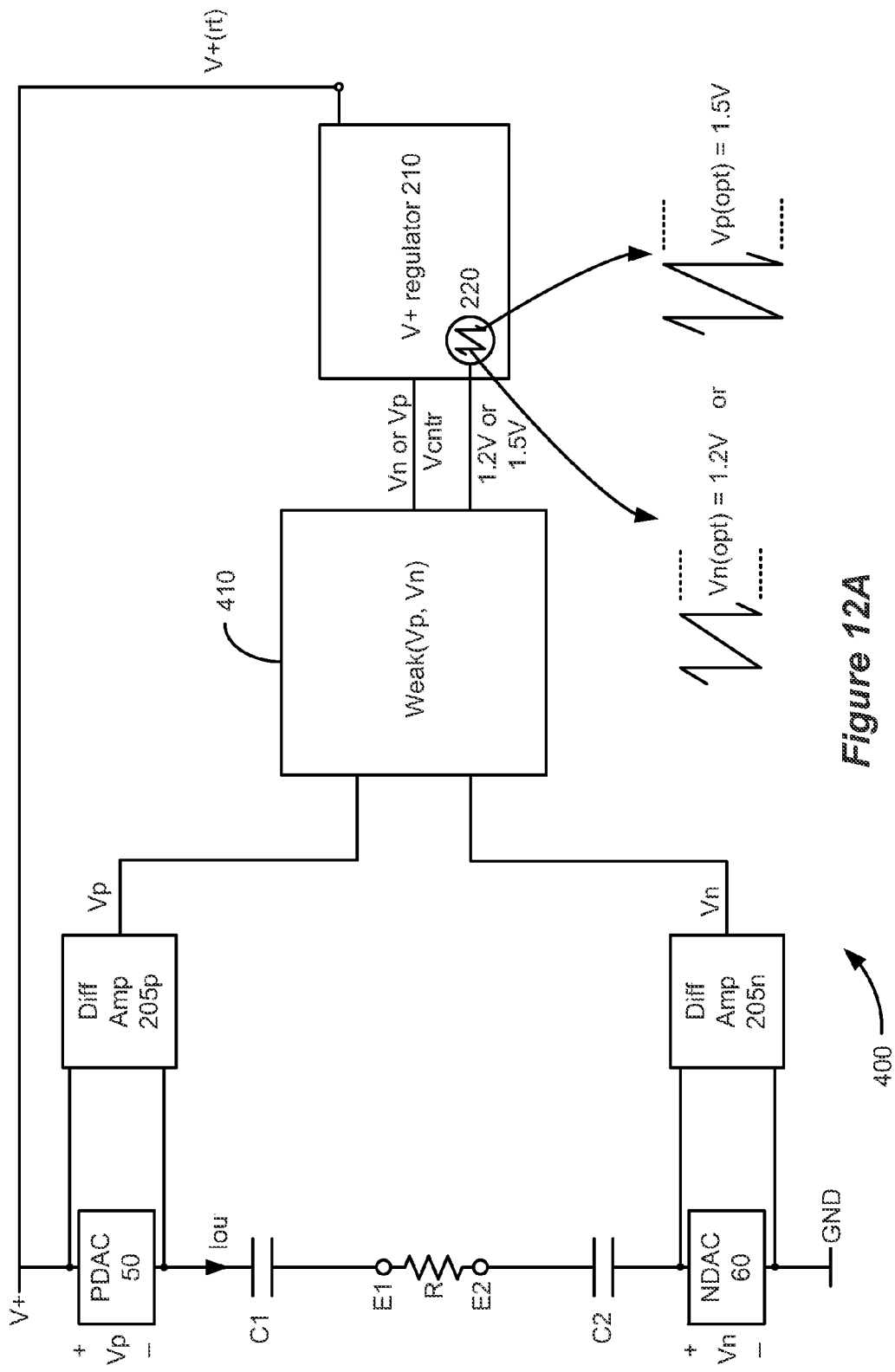
FIG. 12A illustrates the improved compliance voltage generation circuit used in architectures employing a current source and a current sink, and illustrates the compliance voltage being set as a function of the weaker of the two, in accordance with an embodiment of the present invention.

Still, the improved V+ generation circuitry can be modified to ensure that neither of the PDAC 50 or NDAC are running weak, and such modification 400 is shown in FIGS. 12A and 12B. In this version of the improved V+ generation circuitry 400, both of the voltage drops across the PDAC 50 and the NDAC 60, Vp and Vn, are once again monitored in real time, and are used to produce a real time varying compliance voltage V+(rt) that optimally biases both current generators for efficient operation. However, in this example, V+(rt) is established and controlled by the weaker of Vp and Vn. In other words, V+(rt) is set in real time so that neither Vp<Vp(opt)= 1.5V nor Vn<Vn(opt)=1.2V.

FIG. 12A shows the circuitry used, which is largely similar to that shown in FIG. 10A, and thus similar aspects are not again discussed. Different to the embodiment of FIG. 12A is the use of selection circuitry 410. Selection circuitry 410 selects which of Vp or Vn is the weakest relative to its optimal value, and passes that weakest value and its corresponding optimal voltage to the V+ regulator to control V+(rt). The selection circuitry 410 is shown in further detail in FIG. 12B. Vp and Vn are input to the inverting input of differential amplifiers 415 and 420 respectively. The non-inverting inputs are respectively provided with Vp(opt) and Vn(opt), which again can be generated using tunable bandgap reference voltage generators. The diff amps 415 and 420 output the differences in their inputs, and those outputs are provided to a comparator 422, which controls a multiplexer 425. If Vp(opt)−Vp is greater than Vn(out)−Vn, which suggests that the PDAC (Vp) is weaker, then the comparator outputs a 1, and Vp is passed to the V+ regulator 210. If Vn(opt)−Vn is greater than Vp(out)−Vp, which suggests that the NDAC (Vn) is weaker, then the comparator outputs a 0, and Vn is passed to the V+ regulator 210. Thus, the weaker of Vp or Vn at any given time is used to control the V+ regulator 210, which will in turn raise V+(rt) to bring that weaker value back to its optimal level. The output of the comparator 422 is also used to control another multiplexer 430 to send the proper reference voltage, either Vp(opt)=1.5 or Vn(opt)=1.2V to the sawtooth generator 220 so that its maximum value can be set accordingly.

Figure 13:
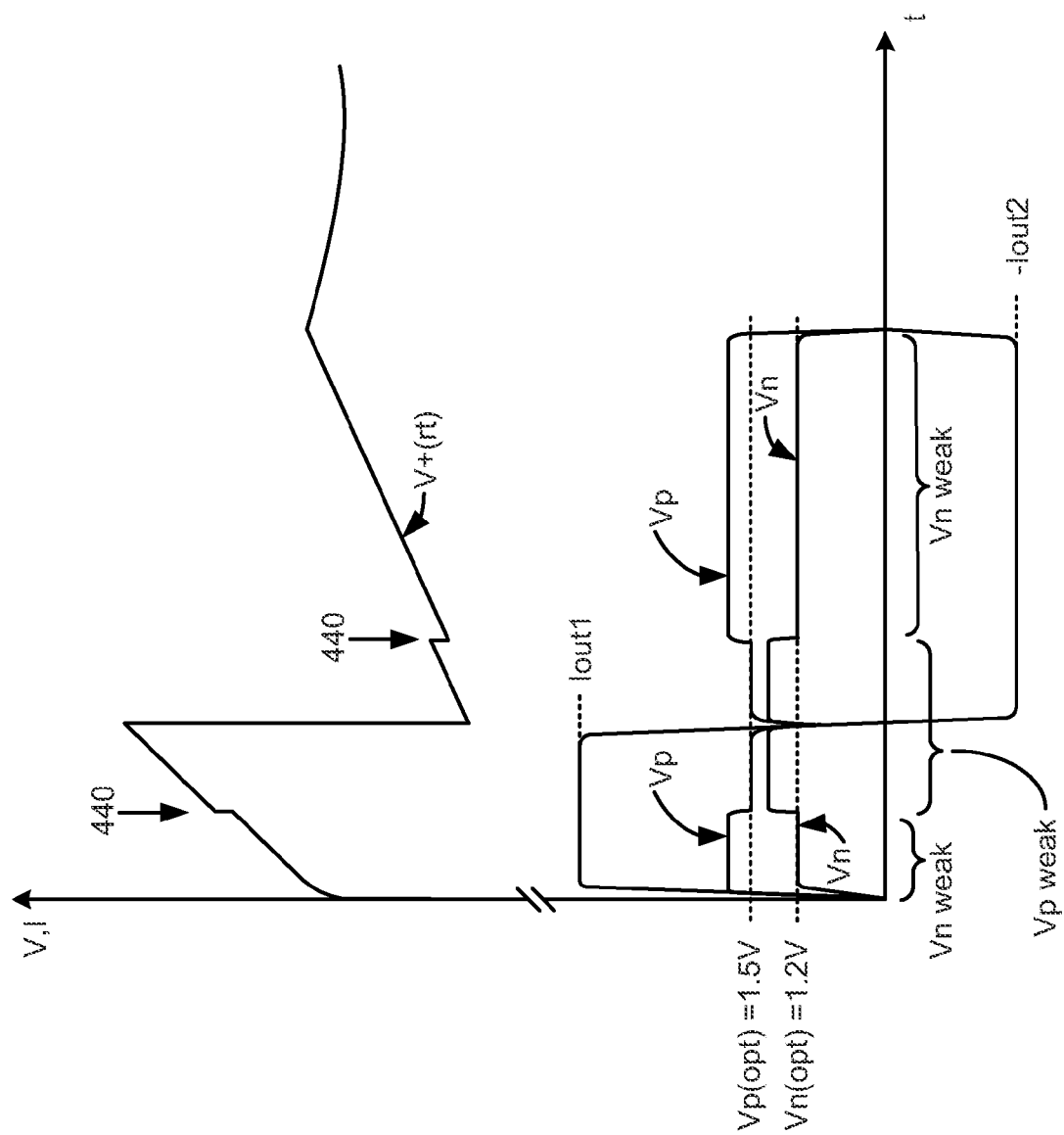
FIG. 13 illustrates waveforms of various voltages generated during the operation of the circuit of FIG. 12A during biphasic current pulses, in accordance with an embodiment of the present invention.

FIG. 13 illustrates the operation of V+ generation circuitry 400. At different times, and for reasons that may not be entirely clear, it is assumed that Vn or Vp is relatively weak. At the beginning of the biphasic pulse, Vn is weak, and thus Vn and Vn(opt) are selected by the selection circuit 410, which brings Vn to Vn(opt)=1.2V. Because Vp is relatively strong, V+(rt) will result in a value for Vp that is higher than optimal, i.e., Vp>Vp(opt). Later, when Vp becomes relatively weak, Vp and Vp(opt) are selected by the selection circuit 410, which brings Vp to Vp(opt)=1.5V. Because Vn is relatively strong at this time, V+(rt) will result in a value for Vn that is higher than optimal, i.e., Vn>Vn(opt). Depending on the relative degrees of weakness during these two periods, V+(rt) may experience discontinuities 440 as it shifts between being controlled by Vp or Vn. In any event, the result is that V+(rt) is established such that neither Vp nor Vn drops below their optimal values Vp(opt) or Vn(opt) at any given time.

The disclosed circuitry is extendable to the control of multiple compliance voltages. Consider FIG. 14A, which has two compliance voltages, V1+ and V2+. As shown, these compliance voltages are used to power two different current paths at the same time, t1. V1+ is used to provide a stimulation current Iout1 from E1 to E2 under the control of PDAC 50a and NDAC 60c; while V2+ is used to provide a stimulation current Iout2 from E3 to E4 under the control of PDAC 50*b* and NDAC 60*d*. Any of the electrodes, PDACs or NDACs could have been chosen for this example.

Figure 14A:
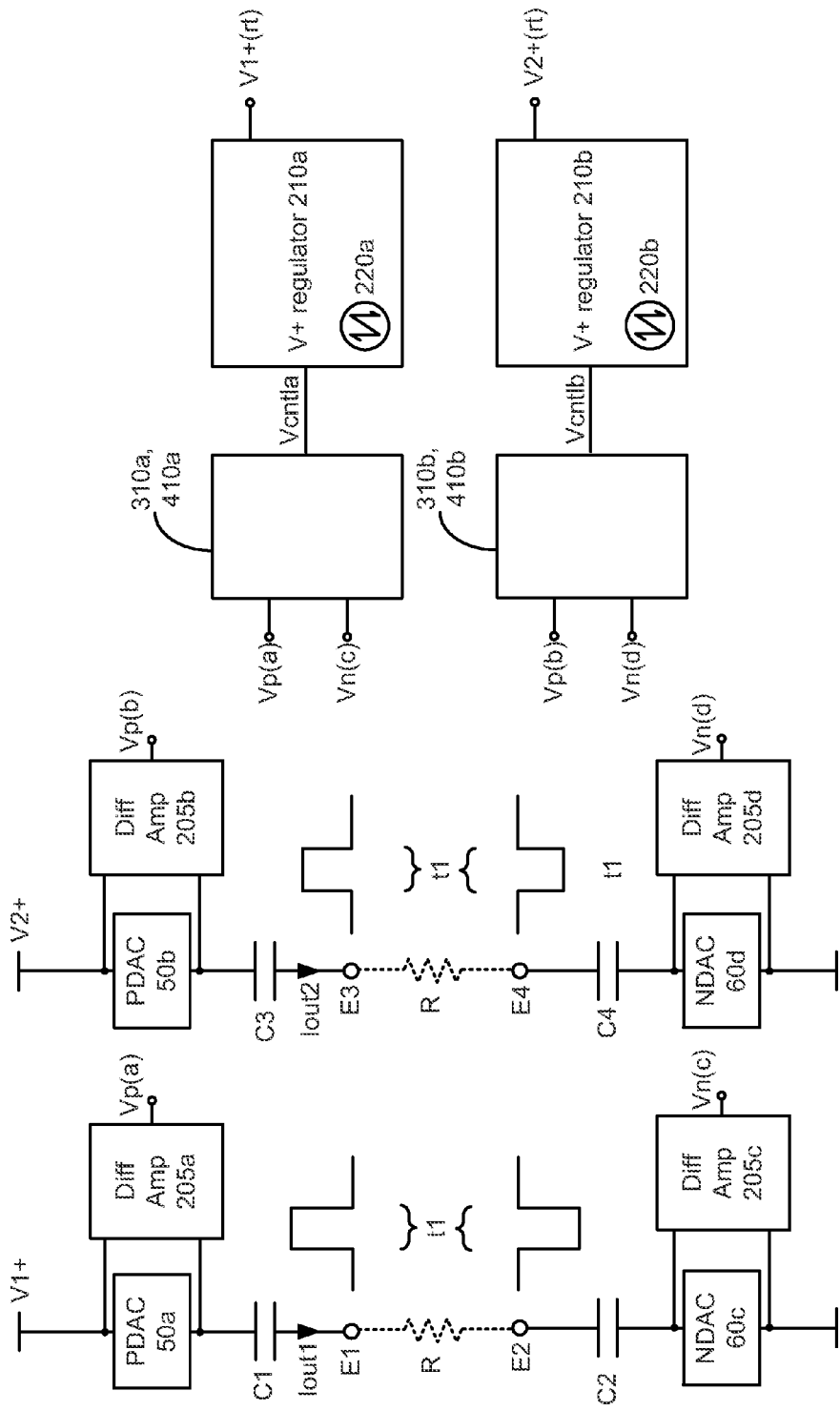
FIG. 14A illustrates multiple compliance voltage generators being used for generating multiple compliance voltages, in accordance with an embodiment of the present invention.

These current paths can be independently controlled, and accordingly, the V+ generation circuitry can be duplicated, as shown in FIG. 14A. Thus, Vp(a) and Vn(c) from the Iout1 current path are input to a first processing block 310*a*, 410*a*, which can comprise either the analog summing circuit 310 of FIG. 10A or the selection circuit 410 of FIG. 12A. The analog control signal Vcntla (either Vp, Vn, or Vp+Vn) is input to a first V+ regulator 210*a* to establish a real-time-varying V1+ (rt) for the Iout1 current path. Likewise, Vp(b) and Vn(d) from the Iout2 current path are input to a second processing block 310*b*, 410*b*, which again can comprise either the analog summing circuit 310 or the selection circuit 410. Analog control signal Vcntlb is input to a second V+ regulator 210*b* to establish a real-time-varying V2+(rt) for the Iout2 current path.

Figure 14B:
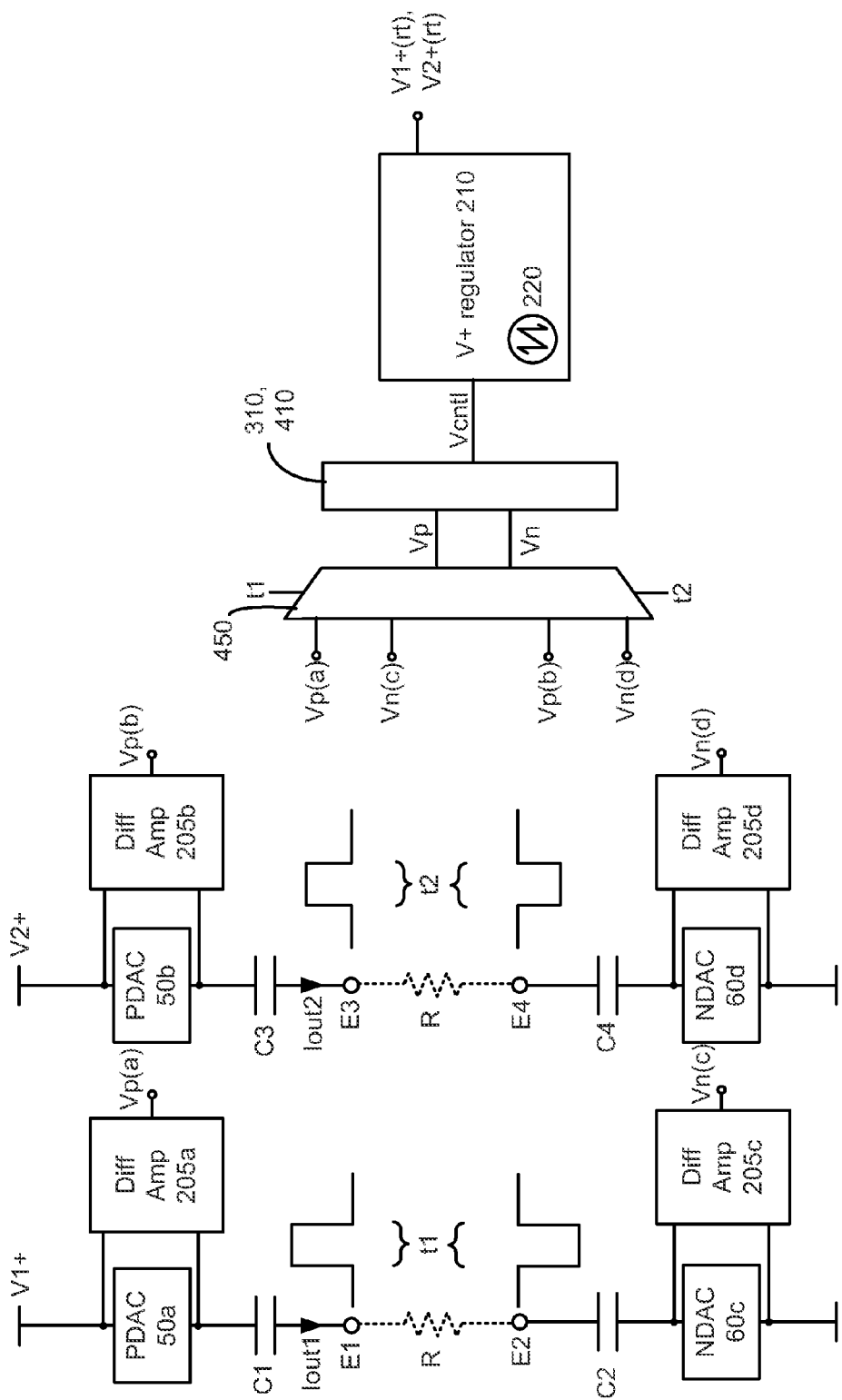
FIG. 14B illustrates one compliance voltage generator circuit being shared to generate multiple compliance voltages, in accordance with an embodiment of the present invention.

FIG. 14B shows a similar example to that illustrated in FIG. 14A, but shows how the V+ generation circuitry can be shared to produce more than one compliance voltage. This example involves the same current paths, but in this instance the pulses do not overlap in time: Iout1 occurs at time t1, while Iout2 occurs at a different time t2. In this example, the V+ generation circuitry can be shared to generate both V1+ and V2+ at different points in time. The various voltage drops across the active DACs (Vp(a), Vp(b), Vn(c), Vn(d)) are input to a multiplexer 450. At time t1, the multiplexer 450 passes Vp(a) and Vn(c) from the Iout1 current path to the V+ generation circuitry to generate V1+(rt). At time t2, the multiplexer 450 passes Vp(b) and Vn(d) from the Iout2 current path to the V+ generation circuitry to generate V2+(rt). Thus, two different and independently tailored compliance voltages are achieved using the same generation circuitry, which is shared at different times.

Figure 15A:
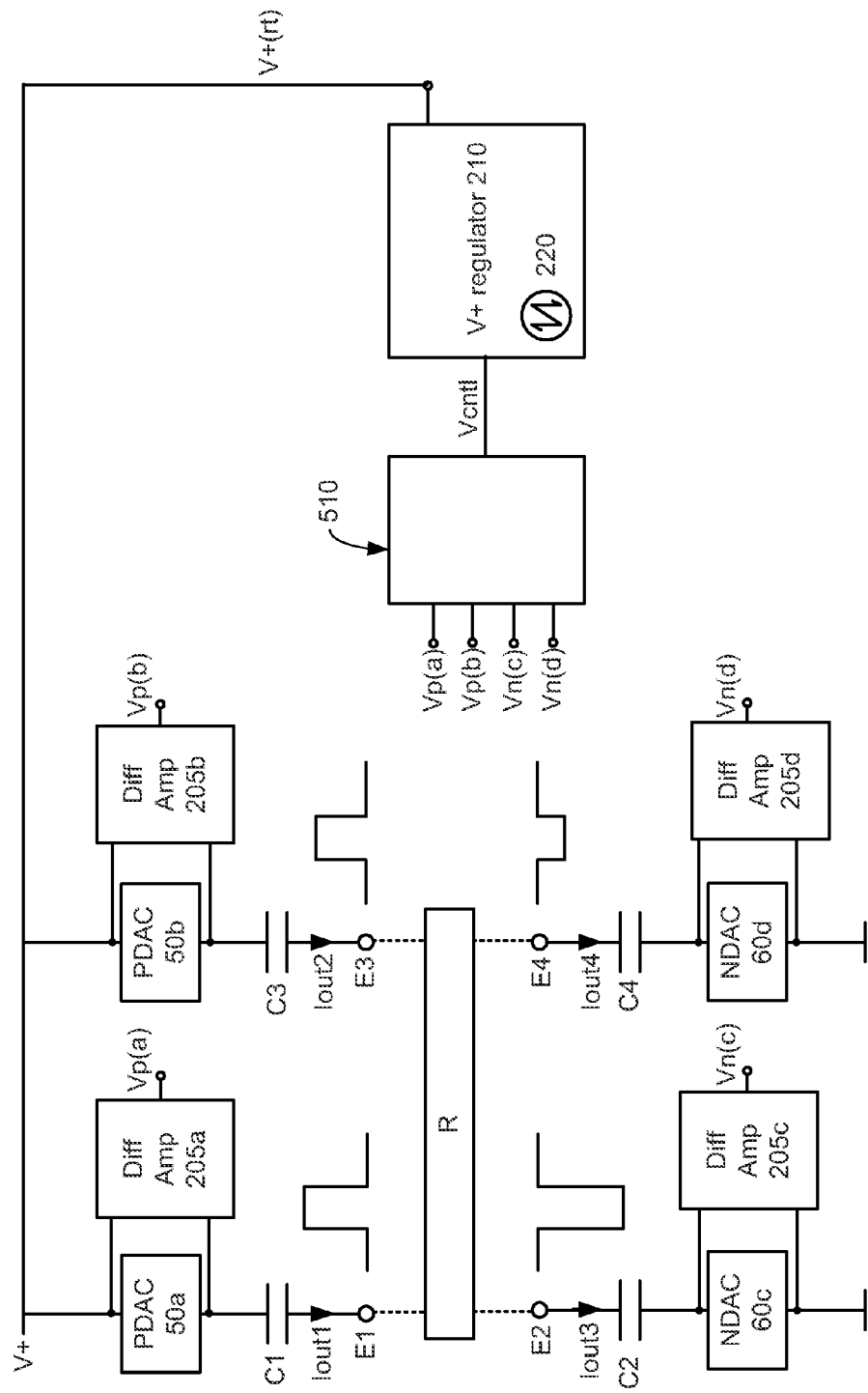
FIG. 15A illustrates the compliance voltage generation circuit being used to generate compliance voltage as a function of more than two current sources and/or more than two current sinks, in accordance with an embodiment of the present invention.

The disclosed circuitry is extendable to the control the compliance voltage even when more than one PDAC and/or more than one NDAC is active at a given time. Consider FIG. 15A, which uses two PDACs (50*a*, 50*b*) to source two different currents (Iout1, Iout2) to electrodes E1 and E3, and which uses two NDACs (60*c*, 60*d*) to sink two different currents (Iout3, Iout4) from electrodes E2 and E4. Again, any of the electrodes, PDACs, or NDACs could have been chosen for this example. (Note also that Iout1+Iout2=Iout3+Iout4 to ensure that the sum of all currents at the tissue equals zero). The voltage drops across the active PDACs and NDACs (Vp (a), Vp(b), Vn(c), Vn(d)) are input to a V+ regulator control circuit 510, which will ultimately generate an analog control signal (Vcntl) for the V+ regulator 210 that is used to set the single compliance voltage V+(rt) for the current distribution circuitry. In FIG. 15A, it is assumed that the voltage drops across the active DACs have been preselected by the control circuitry 510. However, it should be understood that the control circuitry 510 would in fact receive the outputs of the all of differential amplifiers across all of the PDACs and NDACs in the IPG, and then select those of interest that are currently being used to provide a stimulation current. Selection of active DACs for consideration at the control circuitry 510 can be done in any number of ways, and such circuitry is not shown to reduce complexity.

Figure 15B:
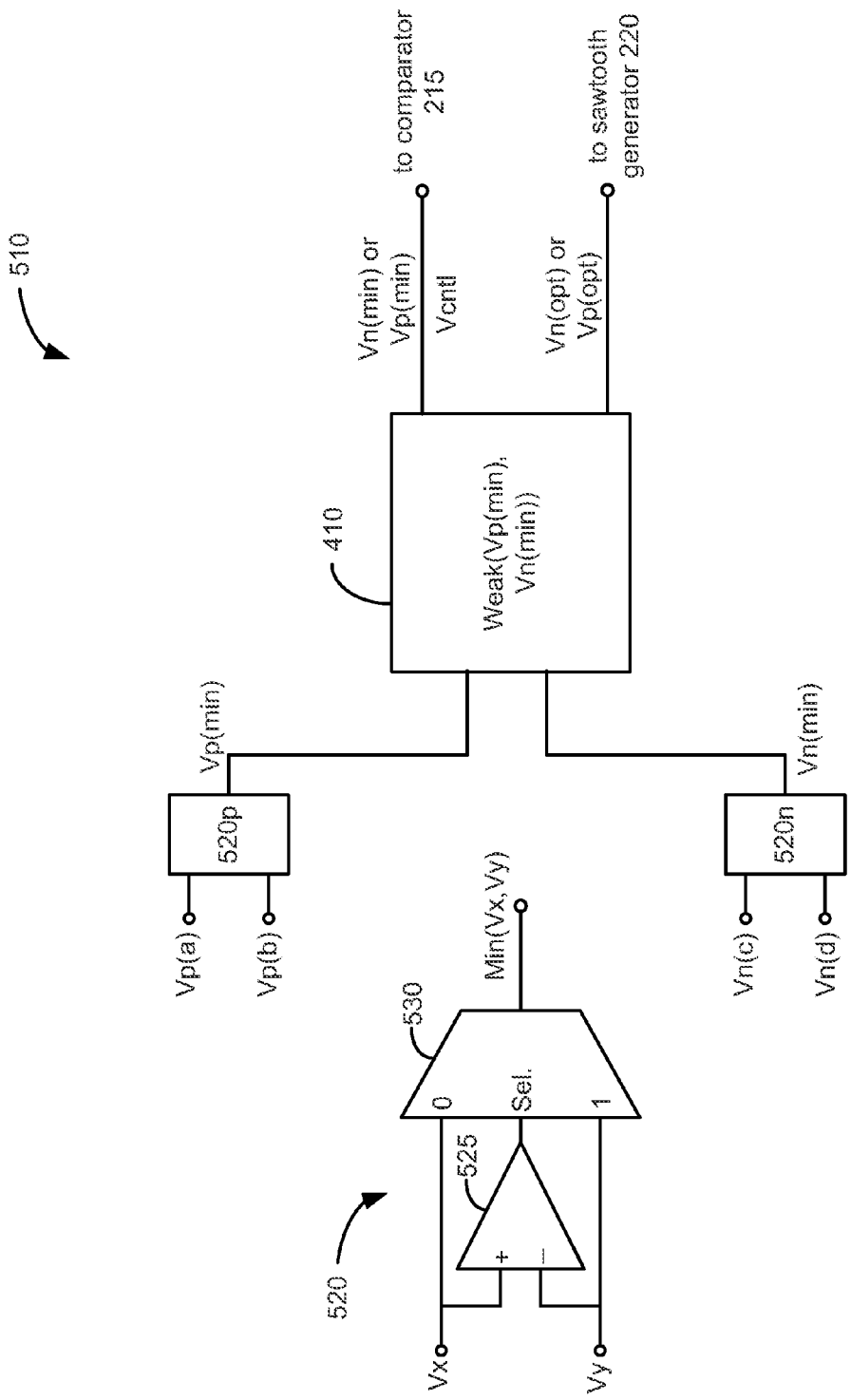
FIG. 15B illustrates the control circuit of FIG. 15A where the compliance voltage is determined based on the voltage across the weakest of all the current generators, in accordance with an embodiment of the present invention.
Figure 15C:
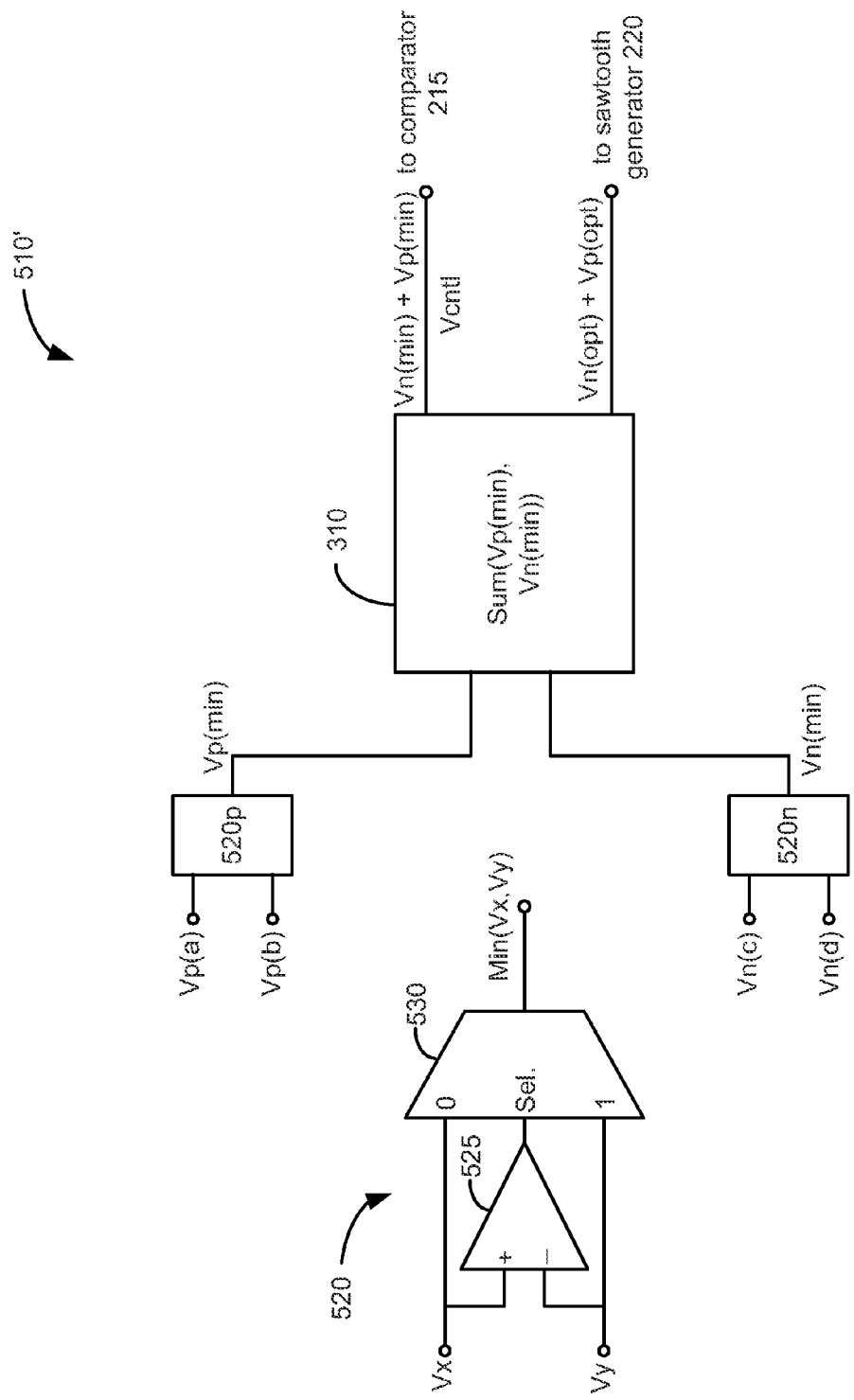
FIG. 15C illustrates the control circuit of FIG. 15A where the compliance voltage is determined based on the sum of voltages across the weakest of the current sources and the current sinks, in accordance with an embodiment of the present invention.

Examples of control circuitry 510 are shown in FIGS. 15B and 15C, and in these examples involve selecting a weakest one of the active PDACs and a weakest one of the active NDACs. In FIG. 15B, the active Vp drops (Vp(a) and Vp(b) in this example) are input to a minimum determining circuit 520*p*. As shown to the left, minimum determining circuit 520 comprises a comparator 525 and a multiplexer 530. If Vx is greater than Vy, the comparator 525 issues a logic '1', and passes Vy to the output. By contrast, if Vx is less than Vy, the comparator 525 issues a logic '0', and passes Vx to the output. In short, 520 passes the smallest of the Vp values to its output (Vp(min)). A similar minimum determining circuit 520 passes the smallest of the Vn values to its output (Vn(min)). It should be understood that a minimum determining circuit 520 can be designed to receive and pass more than two potential inputs, which would be necessary, for example, if three or more PDACs or three or more NDACs are active at any given time. For such a large number of inputs, a cascaded array of minimum determining circuits could be used to identify the minimum values Vp(min) and Vn(min).

The two minimum Vp and Vn values are then sent to selection circuitry 410, which was described earlier with reference to FIG. 12B. By way of review, selection circuitry 410 will choose the weakest of Vp(min) and Vn(min), and use that weakest value as the control voltage (Vcntl) for the V+ regulator 210, thereby assuring that that weakest value (Vp(min) or Vn(min)) is maintained its optimal value (either Vp(opt) or Vn(opt)) by virtue of the V+(rt) feedback loop. As noted earlier, boosting the weakest of the PDACs or NDACs to an optimal value will mean that the voltage drops across the other PDACs or NDACs will be somewhat excessive (>Vp (opt), >Vn(opt)), but it is considered to be a suitable tradeoff and a suitable way to handle regulating V+(rt) based on a number of variables.

An alternative control circuitry 510' for the V+ regulator 210 useable when there are more than one active PDAC and/or NDAC is shown in FIG. 15C. This circuit 510' is similar to circuit 510 of FIG. 15B, and similar aspects will not be discussed again. Different in this circuit 510' is the use of analog summing circuitry 310, which was described earlier with reference to FIG. 10B. By way of review, analog summing circuitry 310 adds (in this case) the weakest of the Vp values to the weakest of the Vn values (Vn(min)+Vp(min)) and uses that sum as the control voltage (Vcntl) for the V+ regulator 210, thereby assuring that the sum of the voltage drops across the weakest PDAC and the weakest NDAC is maintained at an optimal value (Vp(opt)+Vn(opt)) by virtue of the V+(rt) feedback loop. Boosting this weakest PDAC and NDAC to an optimal value will mean that the voltage drops across the other PDACs or NDACs will be somewhat excessive (>Vp(opt), >Vn(opt)), but again this is considered to be a suitable tradeoff and a suitable way to handle regulating V+(rt) based on a number of variables.

Figure 16A:
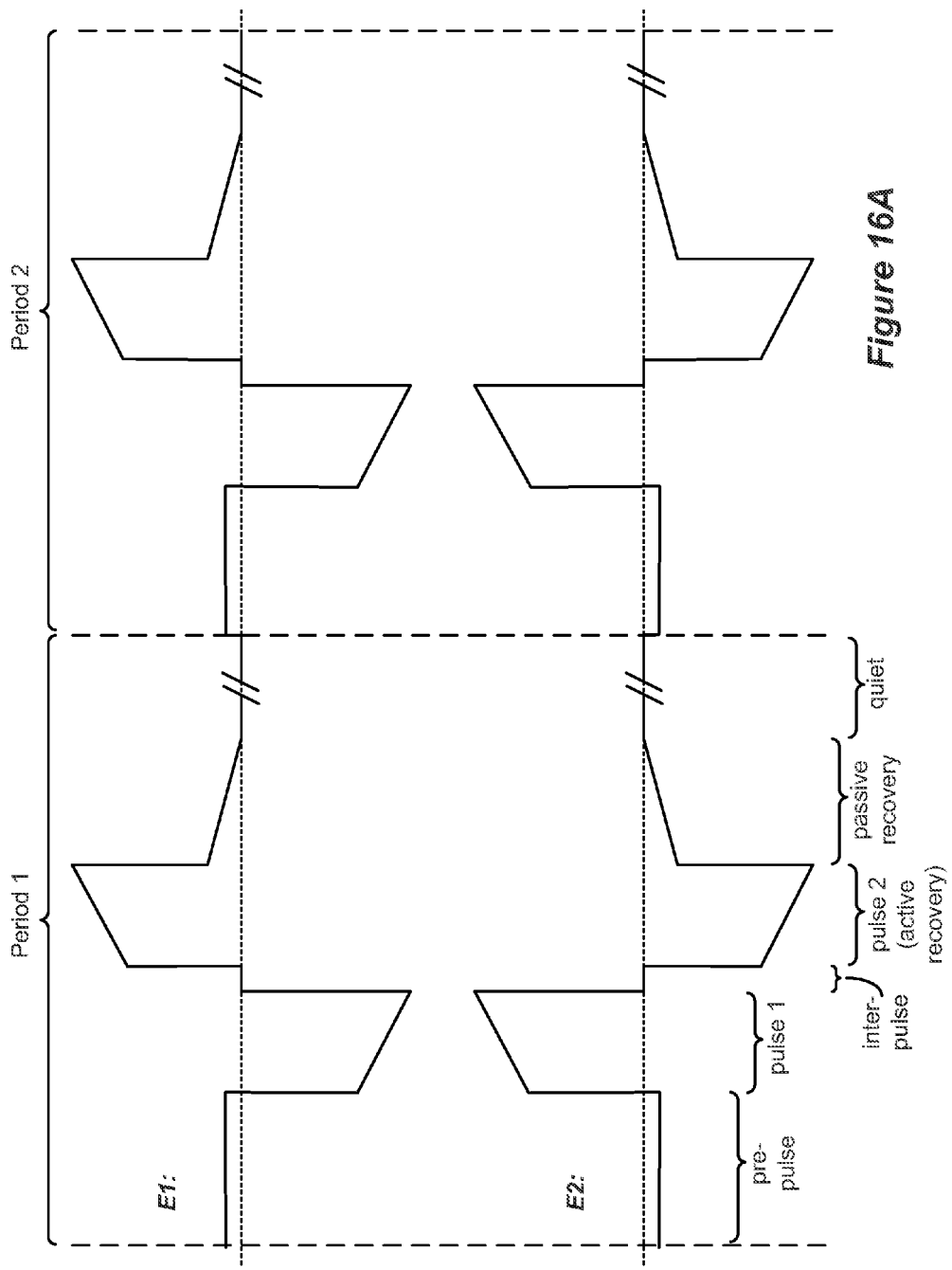
FIGS. 16A and 16B illustrate that the disclosed compliance voltage generation circuitry can be used with stimulation pulses of any shape and form.
Figure 16B:
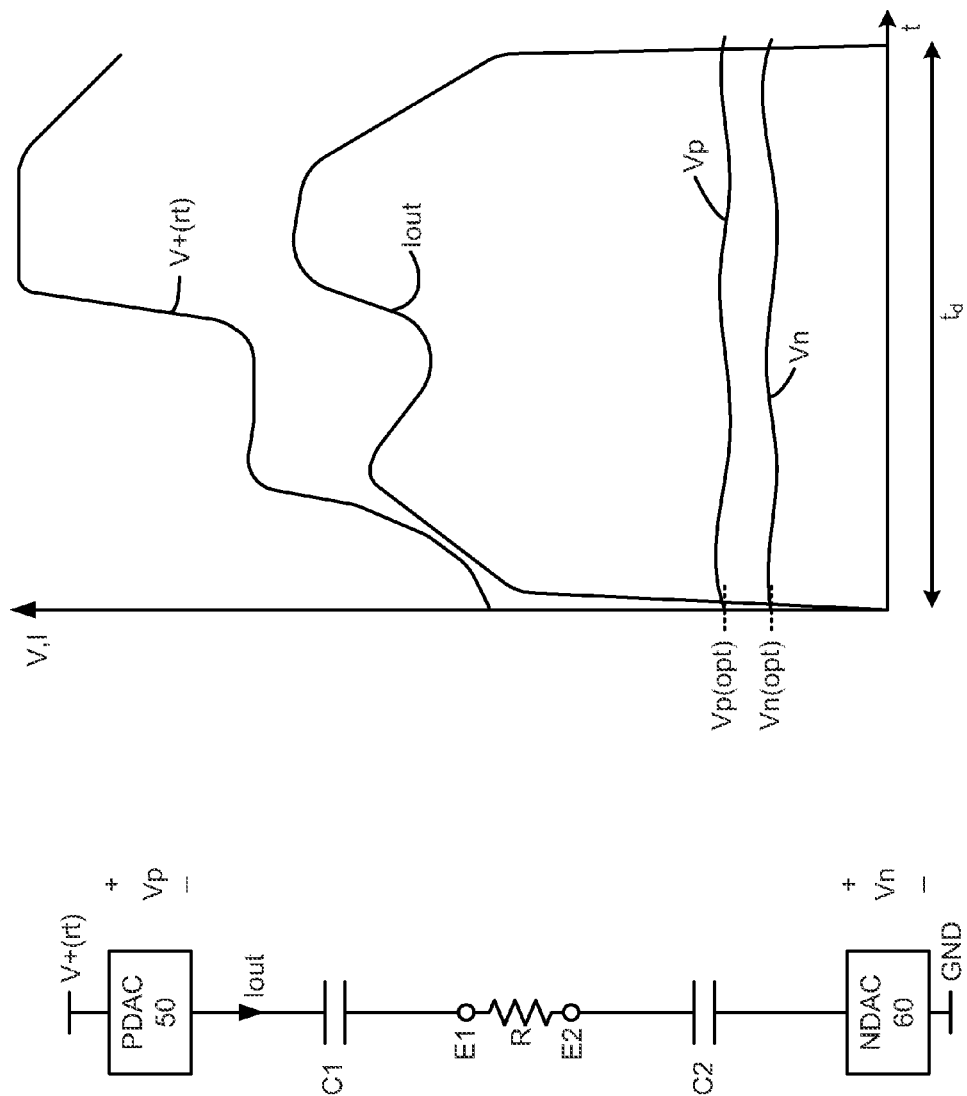

While the preceding discussion illustrated current pulses (uniphasic and biphasic) having constant currents, it should be understood that the real time compliance voltage generation circuitry disclosed can be used with pulses of any shape or form. For example, the stimulation pulses can be ramped as shown in FIG. 16A, and can contain other active pulse phases (such as a pre-pulse phase, a first phase 1, and a second phase 2). Or, the stimulation pulses can take on arbitrary shapes, as shown in FIG. 16B. As long as the compliance voltage generation circuitry is able to monitor the voltages across the active current generators (which could be one or more current generators based on the architecture being employed), the compliance voltage V+(rt) will be adjusted and fed back to the current distribution circuitry to keep the current generator(s) in saturation (i.e., at Vp(opt) and Vn(opt) regardless of the shape of the stimulation current generated by those current generators.

As one skilled in the art will understand, given that the polarity of a current can be viewed differently, "sourcing" and "sinking" of current should be understood as of opposite polarity, but each should not imply any particular polarity.

Thus, sourced current can comprise that provided by the NDACs, and sunk current can comprise that provided by the PDACs.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. Circuitry configured to produce a compliance voltage in an implantable stimulator device, comprising:
a biasing circuit configured to provide a current pulse between at least one first electrode and at least one second electrode, wherein the biasing circuit is connected in series with the at least one first electrode and the at least one second electrode between a time-varying compliance voltage and a reference voltage;
a first amplifier configured to measure a first voltage across the biasing circuit continuously during the current pulse; and
regulator circuitry configured to continuously vary the compliance voltage during the current pulse in accordance with the first voltage,
wherein the regulator circuitry comprises a waveform generator for producing a waveform,
wherein the waveform generator receives a first optimal voltage across the biasing circuit to set a maximum amplitude of the waveform to the first optimal voltage, and
wherein the first voltage is compared to the waveform to provide a gating signal to a pulse width modulation transistor in the regulatory circuitry.

2. The circuit of claim 1, wherein the biasing circuit is connected to the compliance voltage.

3. The circuit of claim 1, wherein the biasing circuit is connected to the reference voltage.

4. The circuitry of claim 1, wherein the regulator circuitry comprises a boost converter.

5. The circuitry of claim 1, wherein the first voltage enables the regulator circuitry to increase the compliance voltage when the first voltage is low compared to the first optimal voltage.

6. The circuitry of claim 5, wherein the first voltage disables the regulator circuitry voltage when the first voltage is high compared to the first optimal voltage, thus allowing the compliance voltage to decrease.

7. The circuitry of claim 1, wherein the current pulse comprises a uniphasic current pulse.

8. The circuitry of claim 1, wherein the current pulse comprises a biphasic current pulse.

9. The circuitry of claim 1, wherein the regulator is configured to continuously vary the compliance voltage during the current pulse to keep the first voltage at a constant value during the current pulse.

10. The circuitry of claim 1, further comprising decoupling capacitors coupled to the at least one first electrode and the at least one second electrode.

11. The circuitry of claim 1, wherein the biasing circuit comprises a source circuit connected to the compliance voltage, wherein the source circuit is configured to source the current pulse to the at least one first electrode, and further comprising
a sink circuit connected to the reference voltage, wherein the sink circuit is configured to sink the current pulse from the at least one second electrode, and
a second amplifier configured to measure a second voltage across the sink circuit continuously during the current pulse.

12. The circuitry of claim 11, wherein regulator circuitry is configured to continuously vary the compliance voltage during the current pulse in accordance with the first and second voltages.

13. The circuitry of claim 12, wherein the regulator circuitry is configured to continuously vary the compliance voltage during the current pulse in accordance with sum of the first and second voltages.

14. The circuitry of claim 12, wherein the regulator circuitry is configured to continuously vary the compliance voltage during the current pulse in accordance with a lower of the first and second voltages relative to the first optimal voltage and a second optimal voltage across the sink circuit.

15. The circuitry of claim 1, wherein the biasing circuit comprises a sink circuit connected to the reference voltage, wherein the sink circuit is configured to sink the current pulse from the at least one second electrode, and further comprising
a source circuit connected to the compliance voltage, wherein the source circuit is configured to source the current pulse to the at least one first electrode, and
a second amplifier configured to measure a second voltage across the source circuit continuously during the current pulse.

16. The circuitry of claim 15, wherein regulator circuitry is configured to continuously vary the compliance voltage during the current pulse in accordance with the first and second voltages, or in accordance with the first or second voltages.

17. The circuitry of claim 16, wherein the regulator circuitry is configured to continuously vary the compliance voltage during the current pulse in accordance with sum of the first and second voltages.

18. The circuitry of claim 16, wherein the regulator circuitry is configured to continuously vary the compliance voltage during the current pulse in accordance with a lower of the first and second voltages relative to the first optimal voltage and a second optimal voltage across the source circuit.

* * * * *